United States Patent
Carr et al.

(10) Patent No.: US 11,246,957 B2
(45) Date of Patent: Feb. 15, 2022

(54) SYSTEMS AND METHODS FOR MAKING HYDROPHILIC FOAMS

(71) Applicant: CURALINE INC., Burr Ridge, IL (US)

(72) Inventors: Roy D. Carr, Burr Ridge, IL (US); Haitham Matloub, Waukesha, WI (US)

(73) Assignee: Newmedical Technology, Inc., Northbrook, IL (US)

( * ) Notice: Subject to any disclaimer, the term of this patent is extended or adjusted under 35 U.S.C. 154(b) by 998 days.

(21) Appl. No.: 15/747,587

(22) PCT Filed: Jul. 28, 2016

(86) PCT No.: PCT/US2016/044490
§ 371 (c)(1),
(2) Date: Jan. 25, 2018

(87) PCT Pub. No.: WO2017/019868
PCT Pub. Date: Feb. 2, 2017

(65) Prior Publication Data
US 2019/0083675 A1 Mar. 21, 2019

Related U.S. Application Data

(60) Provisional application No. 62/197,837, filed on Jul. 28, 2015.

(51) Int. Cl.
*A61L 15/42* (2006.01)
*A61F 13/00* (2006.01)
(Continued)

(52) U.S. Cl.
CPC ............ *A61L 15/425* (2013.01); *A61F 13/00* (2013.01); *A61F 13/00008* (2013.01);
(Continued)

(58) Field of Classification Search
CPC ........ A61L 15/425; A61L 15/26; A61L 15/44; A61L 15/48; A61L 15/56; A61L 15/60;
(Continued)

(56) References Cited

U.S. PATENT DOCUMENTS

| 3,496,043 A * | 2/1970 | Ragan ................... B29D 16/00 156/210 |
| 4,157,416 A * | 6/1979 | Cobb ....................... B32B 5/24 428/420 |

(Continued)

FOREIGN PATENT DOCUMENTS

| WO | 2003097727 A1 | 11/2003 | |
| WO | WO 2003/097727 A1 * | 11/2003 | ................ C08J 9/08 |

OTHER PUBLICATIONS

PCT International Search Report in International Application No. PCT/US2016/044490 dated Dec. 8, 2016.

*Primary Examiner* — Philip R Wiest
(74) *Attorney, Agent, or Firm* — Greenberg Traurig, LLP; David J. Dykeman; Roman Fayerberg

(57) ABSTRACT

Provided herein are methods for making foam materials and foam material products having a polyurethane foam matrix defining a plurality of pores, a hydrophilic agent retained within at least a portion of the pores for improving an absorption of the foam material, a salt retained within at least a portion of the pores in an amount sufficient to render the foam material isotonic, a surfactant retained within at least a portion of the pores in an amount sufficient to be released upon contact with a moist surface. Also provided herein are methods for making a multilayer foam by casting a second foam layer on a first foam layer substrate and compressing the second foam layer before the second layer is fully cured to form an interface layer in situ.

5 Claims, 18 Drawing Sheets

(51) Int. Cl.

| | | |
|---|---|---|
| *A61L 15/26* | (2006.01) | |
| *A61L 15/44* | (2006.01) | |
| *A61L 15/48* | (2006.01) | |
| *A61L 15/56* | (2006.01) | |
| *A61L 15/60* | (2006.01) | |
| *A61F 13/02* | (2006.01) | |
| *B32B 3/30* | (2006.01) | |
| *B32B 5/18* | (2006.01) | |
| *B32B 5/32* | (2006.01) | |
| *B32B 27/06* | (2006.01) | |
| *B32B 27/40* | (2006.01) | |
| *A61K 36/00* | (2006.01) | |
| *A61F 13/40* | (2006.01) | |

(52) U.S. Cl.
CPC .. *A61F 13/00017* (2013.01); *A61F 13/00025* (2013.01); *A61F 13/00029* (2013.01); *A61F 13/00042* (2013.01); *A61F 13/00046* (2013.01); *A61F 13/00059* (2013.01); *A61F 13/00063* (2013.01); *A61F 13/00995* (2013.01); *A61F 13/02* (2013.01); *A61L 15/26* (2013.01); *A61L 15/44* (2013.01); *A61L 15/48* (2013.01); *A61L 15/56* (2013.01); *A61L 15/60* (2013.01); *B32B 3/30* (2013.01); *B32B 5/18* (2013.01); *B32B 5/32* (2013.01); *B32B 27/065* (2013.01); *B32B 27/40* (2013.01); *A61K 36/00* (2013.01); *A61L 2300/404* (2013.01); *A61L 2300/442* (2013.01); *A61L 2400/08* (2013.01); *A61M 35/006* (2013.01); *B32B 2266/0278* (2013.01); *B32B 2307/728* (2013.01); *B32B 2535/00* (2013.01)

(58) Field of Classification Search
CPC ......... A61L 2300/404; A61L 2300/442; A61L 2400/08; A61F 13/00; A61F 13/00008; A61F 13/00017; A61F 13/00025; A61F 13/00029; A61F 13/00042; A61F 13/00046; A61F 13/00059; A61F 13/00063; A61F 13/00995; A61F 13/02; B32B 3/30; B32B 5/18; B32B 5/32; B32B 27/065; B32B 27/40; B32B 2266/0278; B32B 2307/728; A61M 26/006

See application file for complete search history.

(56) References Cited

U.S. PATENT DOCUMENTS

| | | | |
|---|---|---|---|
| 5,064,653 | A | 11/1991 | Sessions et al. |
| 5,065,752 | A | 11/1991 | Sessions et al. |
| 5,254,301 | A | 10/1993 | Sessions et al. |
| 5,296,228 | A | 3/1994 | Chang et al. |
| 5,916,928 | A * | 6/1999 | Sessions ............... B29C 44/321 521/155 |
| 2004/0034058 | A1* | 2/2004 | Armour ................. A61P 11/06 514/317 |
| 2005/0013987 | A1 | 1/2005 | Carr et al. |
| 2006/0293205 | A1* | 12/2006 | Chung ................ C11D 17/049 510/383 |
| 2008/0131493 | A1 | 6/2008 | Matloub |
| 2011/0275972 | A1 | 11/2011 | Rosenberg et al. |
| 2012/0015161 | A1 | 1/2012 | Todt et al. |

\* cited by examiner

300

```
┌─────────────────────────────────────┐
│   Providing a first foam layer.     │
│              301                    │
└─────────────────────────────────────┘
                 │
                 ▼
┌─────────────────────────────────────┐
│ Casting a second foam layer on the  │
│         first foam layer.           │
│              303                    │
└─────────────────────────────────────┘
                 │
                 ▼
┌─────────────────────────────────────┐
│   Compressing the second foam layer.│
│              305                    │
└─────────────────────────────────────┘
                 │
                 ▼
┌─────────────────────────────────────┐
│ Curing the second foam layer to     │
│      form a multilayer foam.        │
│              307                    │
└─────────────────────────────────────┘
```

FIG. 3

| Sample ID | Absorption Rate, seconds | Thickness inches | Density pcf | Sample weight, grams | Maximum absorption weight, grams | Weight after compression, grams | Total absorbed, grams | Times original weight absorbed | Tightly bound absorbed, grams | Times original weight tightly bound | Viscosity of Slurry used to prepare foam, cPs |
|---|---|---|---|---|---|---|---|---|---|---|---|
| Core dressing 03012012 | 1 | 0.125 | 9.8 | 0.32 | 6.27 | 4.00 | 5.95 | 18.6x | 3.68 | 11.5x | 1900 |
| 02142013-1, lactated Ringer's Solution | 2 | .125 | 11.9 | .39 | 7.69 | 5.43 | 7.30 | 18.7x | 5.04 | 12.9x | 2400 |
| 02142013-2, lactated Ringer's Solution | 2 | .094 | 12.6 | .31 | 5.46 | 3.82 | 5.15 | 16.6x | 3.51 | 11.3x | 2400 |
| 02162013-1, Ringer's Solution non- | 2 | .094 | 12.2 | .3 | 5.22 | 3.70 | 4.92 | 16.4x | 3.40 | 11.3x | 2500 |
| 02162013-2, Ringer's Solution non- | 2 | .094 | 11.3 | .28 | 4.81 | 3.48 | 4.53 | 16.2x | 3.20 | 11.4x | 2500 |
| 02152013, Zero salt slurry | 4 | .063 | 14.5 | .24 | 2.09 | 0.64 | 1.85 | 7.7 | 0.40 | 1.7x | 1850 |

FIG. 9A

| Sample ID | Absorption Rate, seconds | Thickness inches | Density, pcf | Sample weight, grams | Maximum absorption weight, grams | Weight after compression, grams | Total absorbed, grams | Times original weight absorbed | Tightly bound absorbed grams | Times original weight tightly bound |
|---|---|---|---|---|---|---|---|---|---|---|
| 3M Foam | 1 | .22 | 7.0 | .3 | 4.1 | 1.1 | 3.8 | 12.7 | 0.8 | 2.7 |
| Molnlycke Mepilex | >60 | .19 | 10.1 | .5 | 6.1 | 1.1 | 5.6 | 11.2 | 0.6 | 1.2 |
| Smith & Nephew Allevyn | >60 | .22 | 7.0 | .4 | 6.0 | 1.2 | 5.6 | 14 | 0.8 | 2.0 |
| Invention | 2 | .19 | 10.1 | .5 | 11.0 | 7.0 | 10.5 | 21 | 6.5 | 13 |
| Ferris Polymem | 2 | 0.10 | 11.4 | .3 | 3.9 | 2.3 | 3.6 | 12 | 2.0 | 6.7 |
| Medline Optifoam nonadhesiv | 2 | 0.156 | 13.2 | .54 | 6.31 | 1.60 | 5.77 | 10.7 | 1.06 | 1.96 |

FIG. 9B

| Sample ID | Absorption Rate, seconds | Thickness inches | Density pcf | Sample weight, grams | Maximum absorption weight, grams | Weight after compression, grams | Total absorbed, grams | Times original weight absorbed | Tightly bound absorbed, grams | Times original weight tightly bound |
|---|---|---|---|---|---|---|---|---|---|---|
| Core dressing 03012012 | 1 | 0.125 | 9.8 | 0.32 | 6.27 | 4.00 | 5.95 | 18.6x | 3.68 | 11.5x |
| 1% ZnO 03022012-1 | 1 | .156 | 8.8 | .36 | 7.8 | 4.44 | 7.44 | 20.7 | 4.08 | 11.3 |
| 1% ZnO 2% CHG 0302012-2 | 2 | .125 | 10.7 | .35 | 6.89 | 3.66 | 6.54 | 18.7 | 3.31 | 9.5 |
| 0.5% CHG 03022012-3 | 1 | .125 | 10.1 | .33 | 6.38 | 3.78 | 6.05 | 18.3 | 3.45 | 10.5 |
| 2% CHG 03022012-4 | 1 | .156 | 9.8 | .40 | 8.94 | 5.03 | 8.54 | 21.4 | 4.63 | 11.6 |
| 6% Povidone iodine 03042012 | 2 | .188 | 9.1 | .45 | 9.22 | 5.41 | 8.77 | 19.5 | 4.96 | 11.0 |

FIG. 9C

| Component | #1 (core slurry formula) | #2 | #3 | #4 | #5 |
|---|---|---|---|---|---|
| Water | 80 grams | 80 | 80 | 80 | 80 |
| NaCl | 1.13 | 0.19 | 5.06 | 1.04 | 0.98 |
| SAP 1161 | 15.2 | 15.05 | 15.01 | 45.65 | 4.99 |
| Ratio NaCl:SAP | 1:15 | 1:75 | 1:3 | 1:4.5 | 1:5 |
| Ratio SAP:H2O | 1:5.3 | 1:5.3 | 1:5.3 | 1:1.8 | 1:16 |
| Viscosity, cPs | 2020 | 3330 | 1100 | Not measurable, solid | 200 |

FIG. 9D

SYSTEMS AND METHODS FOR MAKING HYDROPHILIC FOAMS

CROSS-REFERENCE AND CLAIM OF PRIORITY TO RELATED APPLICATIONS

This application is a U.S. national phase application of PCT International Patent Application No. PCT/US2016/044490, filed on Jul. 28, 2016, which claims benefit of and priority to U.S. Provisional Patent Application 62/197,837, entitled "Novel Physiologic Loaded Single and Multi-Layered Cast Polyurethane Foam Compositions", filed on Jul. 28, 2015, the contents of each of which are incorporated herein in their entireties.

FIELD

The present disclosure relates to compositions and methods for making foam and more particularly to single or multiple layer hydrophilic foams.

BACKGROUND

Absorbent pads have variety of uses and are made from diverse materials. Such pads can, for example, be used to contact the skin for absorbing body fluids. Generally, conventional absorbent pads are capable of absorbing moisture or fluids from an adjacent site. However, conventional absorbent pads also exhibit difficulty retaining the absorbed fluids. For example, in the context of a wound dressing, absorbed fluids can leak or discharge from an absorbent pad when the pad contacted by a patient, care provider, bed, furniture, or otherwise, thus requiring changing of the dressing and cleaning of the patient, care giver, bed linens, etc.

SUMMARY

Provided herein are improved compositions and methods for making hydrophilic foams.

In some embodiments, a foam material is provided. The foam material includes a polyurethane foam matrix defining a plurality of pores. The foam material also includes a hydrophilic agent retained within at least a portion of the pores for improving an absorption of the foam material. The foam material also includes a salt retained within at least a portion of the pores in an amount sufficient to render the foam material isotonic. The foam material also includes a surfactant retained within at least a portion of the pores in an amount sufficient to be released upon contact with a moist surface.

In some embodiments, a multilayer foam is provided. The multilayer foam includes a first layer of foam material. The first layer of foam material includes a first polyurethane foam matrix defining a plurality of first pores. The first layer of foam material also includes a first hydrophilic agent retained within at least a portion of the first pores for improving an absorption property of the foam material. The first layer of foam material also includes a first salt retained within at least a portion of the first pores in an amount sufficient to render the first layer of foam isotonic. The first layer of foam material also includes a first surfactant retained within at least a portion of the first pores in an amount sufficient to be released upon contact between the first layer and a moist surface. The multilayer foam also includes one or more secondary layers of foam material. Each secondary layer includes a secondary polyurethane foam matrix defining a secondary plurality of pores. Each secondary layer also includes a secondary hydrophilic agent retained within at least a portion of the secondary pores for improving an absorption property of the foam material. Each secondary layer also includes a secondary salt retained within at least a portion of the secondary pores in an amount sufficient to render the secondary layer of foam isotonic. Each secondary layer also includes a secondary surfactant retained within at least a portion of the secondary pores in an amount sufficient to be released upon contact between the secondary layer and a moist surface. The multilayer foam also includes one or more interface layers each bonding at least one of the first layer and one of the secondary layers or bonding adjacent secondary layers, each interface layer including compressed or collapsed polyurethane foam matrix from at least one of the first layer or the one or more secondary layers.

In some embodiments, a foam material comprising the in situ reaction product of a reactant composition is provided. The reactant composition includes an isocyanate-capped polymer-ether prepolymer. The reactant composition also includes a salt. The reactant composition also includes a hydrophilic agent. The reactant composition also includes water.

In some embodiments, a method of preparing a foam material sheet is provided. The method includes mixing a salt with a hydrophilic agent in water forming a slurry. The method also includes admixing a water reactive prepolymer forming a foam reaction product. The method also includes depositing the reaction product on a substrate. The method also includes allowing the reaction product to begin rising. The method also includes compressing the rising reaction product to a desired thickness. The method also includes allowing the reaction product, after compressing, to rise to provide a porous cellular foam sheet of a predetermined thickness. The method also includes compressing the foam after rising for uniform thickness. The method also includes curing the foam sheet.

In some embodiments, a method of controlling the breathability of a layered foam dressing is provided. The method includes forming a first foam layer having a first thickness. The method also includes forming a second layer of a second thickness. The method also includes applying the second foam layer onto the first foam layer creating a layered foam composition having a third thickness. The method also includes contacting the second foam layer to the first foam layer forming an interface layer where the second foam layer contacts the first foam layer. The method also includes controlling the breathability of the first, second and interface layers by compressing the first, second, and interface layer to a fourth thickness before curing the layered composition. The method also includes curing the layered composition. The method also includes drying the layered composition.

In some embodiments a method of forming a foam dressing is provided. The method includes providing a substrate. The method also includes depositing components of a first foam layer onto the substrate. The method also includes mixing the components forming a creaming liquid. The method also includes leveling and spreading the creaming liquid to form a tacky gel. The method also includes leveling and spreading the tacky gel to form a tack free foam. The method also includes allowing the tack free foam to rise. The method also includes compressing the foam after it is fully risen but not fully cured to a predetermined thickness. The method also includes heating the compressed foam, wherein the compressed foam is wet. The method also includes curing and drying the wet foam for form a moist foam. The method also includes drying the moist foam to form the foam dressing.

In some embodiments a composition for making foam is provided. The composition includes an isocyanate-capped polymer-ether prepolymer. The composition also includes a salt. The composition also includes a hydrophilic agent. The composition also includes water.

In some embodiments a multilayer assembly is provided. The multilayer assembly includes a first layer of foam material including a first polyurethane foam matrix defining a plurality of first pores. The multilayer assembly also includes a first surface of the first layer having a plurality of open first pores defined thereon. The multilayer assembly also includes an inclusion retained within at least one of the plurality of open first pores. The multilayer assembly also includes a second layer of foam material including a second polyurethane foam matrix defining a plurality of second pores. The multilayer assembly also includes a mating surface of the second layer. The multilayer assembly also includes an interface layer bonding the first surface of the first layer to the mating surface of the second layer, the interface layer including compressed or collapsed polyurethane foam matrix from at least one of the first polyurethane foam matrix and the second polyurethane matrix.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 3 is a flow diagram illustrating a method for forming a multilayer foam in accordance with various embodiments.

FIGS. 9A-9D are tables showing experimental data associated with foam layer compositions in accordance with various embodiments.

Figure 1:
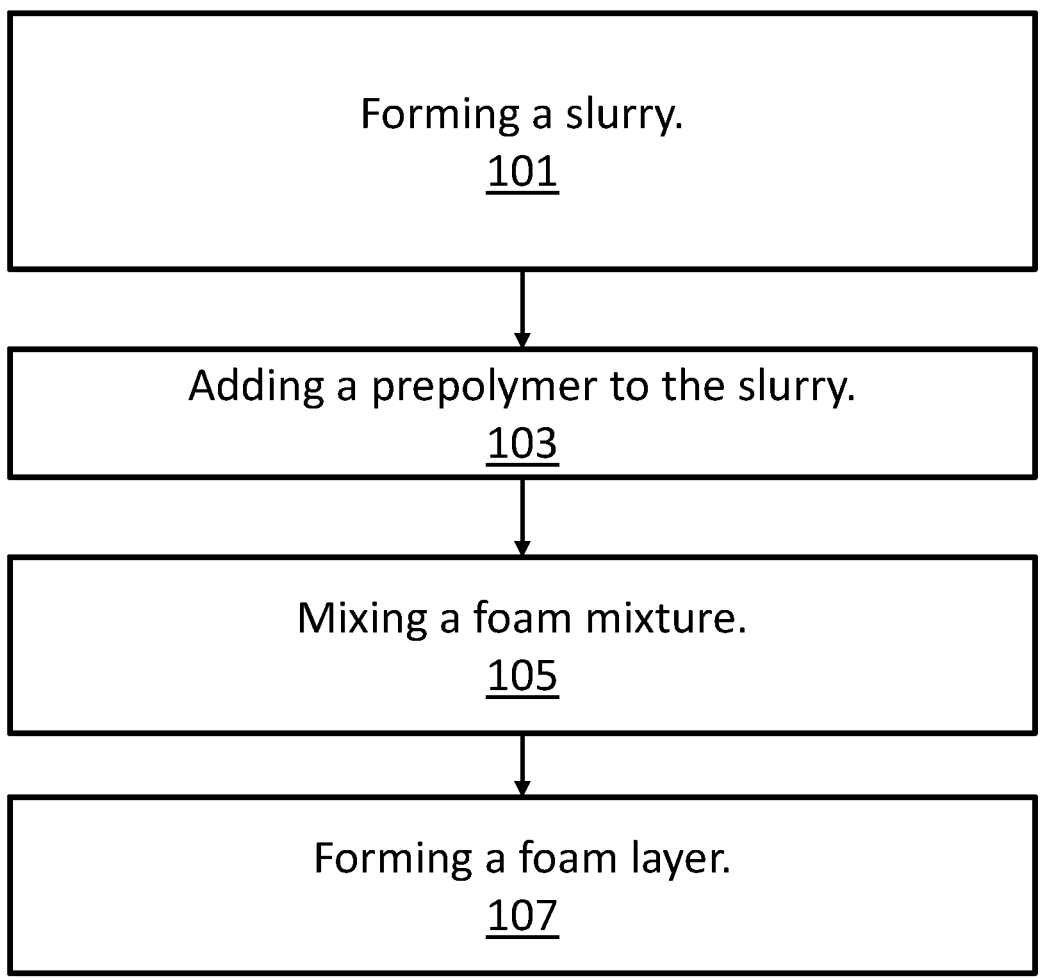
FIG. 1 is a flowchart illustrating a method for forming a foam layer in accordance with various embodiments.

While the above-identified drawings set forth present disclosure, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the present disclosure.

DETAILED DESCRIPTION

In accordance with various embodiments, improved compositions and methods for making hydrophilic foams are provided. The compositions and methods, in accordance with various embodiments can include a foam layer formed by casting or extruding a mixture of a prepolymer with a slurry of water, a salt, a hydrophilic agent, and at least one of a wetting agent or a surfactant. The slurry, in accordance with various embodiments, can also include an adjuvant releasable from the foam in the presence of an external fluid or other additives.

In accordance with various embodiments, the improved compositions and methods can include forming a multilayer foam by bonding two foam layers together. In accordance with various embodiments the bonding can be performed by casting the second foam layer on top of the first foam layer. In accordance with various embodiments, controlled compression rolling of the multilayer foam during casting of the second foam layer on top of the first foam layer can form, in-situ, an interface layer between the first and second layers. In accordance with various embodiments, a moisture vapor transmission rate (MVTR) of the interface layer can be controlled by adjustment of the compression rolling parameters.

In accordance with various embodiments, the foam layer is formed as a highly absorbent hydrophilic polyurethane foam composition that absorbs copious amounts of an external liquid, for example, a fluid or exudate from a wound on the skin, and retain the external liquid for long periods of time. For example, a foam composition in accordance with various embodiments can contain an isocyanate-capped polyether prepolymer and a slurry comprising a physiologic salt, a hydrophilic agent or superabsorbent agent, a mono or polyhydric alcohol, a wetting agent or surfactant, a microbial agent, a skin emollient, and optionally other ingredients, for example, an essential oil, herbals, healing agents and dyes. The hydrophilic polyurethane foam composition not only absorbs copious amounts of an external liquid, in accordance with various embodiments, the foam layer composition can also retain the liquid for long periods of time because, in accordance with various embodiments, the foam layer composition can tightly bind external fluids, for example, over 10 times its original weight.

Furthermore, the example foam compositions described herein can, in accordance with various embodiments, result in a physiologic or isotonic polyurethane foam wound care dressing loaded with wound healing agents of various types or combinations. As used herein, isotonic refers to a material having a same osmotic pressure as a body fluid. As used herein, physiologic refers to a material having a same concentration of electrolytes (e.g., sodium, potassium, calcium) as a body fluid. As will be understood in view of this disclosure, physiologic and/or isotonic materials can be more favorable to tissue and body fluid interaction than non-isotonic or non-physiologic. In particular, no (or very low) salt gradients are created with isotonic and physiologic materials or solutions when they contact body tissue or interact with body fluids.

The physiologic or isotonic character of the physiologic or isotonic polyurethane foam advantageously provides a combination of physiological salts that can permit an aqueous mixture of very large amounts of superabsorbent polymers (SAP) to be fluid enough to be flowable, thereby permitting distribution and retention within the foam. By permitting the large additions of SAP, the physiological salts can, in accordance with various embodiments, permit the resulting foam layer to be more absorbent and have an increased capability for tightly holding wound exudates such as blood, serum, liquefied necrotic tissue and bacteria-containing fluid, before the mixture gels and is immovable or too viscous to be pumpable.

In accordance with various embodiments, improved compositions and methods for making hydrophilic foams are provided. The compositions and methods, in accordance with various embodiments can include a foam layer formed by casting or extruding a mixture of a prepolymer with a slurry of water, a salt, a hydrophilic agent, and at least one of a wetting agent or a surfactant. The slurry, in accordance with various embodiments, can also include an adjuvant releasable from the foam in the presence of an external fluid or other additives.

In accordance with various embodiments, the improved compositions and methods can include forming a multilayer foam by bonding two foam layers together. In accordance with various embodiments the bonding can be performed by casting the second foam layer on top of the first foam layer. In accordance with various embodiments, controlled compression rolling of the multilayer foam during casting of the second foam layer on top of the first foam layer can form, in-situ, an interface layer between the first and second layers. In accordance with various embodiments, a moisture vapor transmission rate (MVTR) of the interface layer can be controlled by adjustment of the compression rolling parameters.

The compositions described herein, in accordance with various embodiments, can permit all of the slurry components to be mixed together with a water reactive prepolymer in the foaming state, thereby rendering additional expensive processing steps unnecessary. Additionally, in accordance with various embodiments, by incorporating agents into the foam itself, the resulting product can be cuttable without ingredients falling out of the foam or being exposed.

Referring now to FIG. 1, a method 100 is provided for forming a foam layer in accordance with various embodiments. The method 100 includes a step of forming a slurry. The method 100 also includes a step of adding 103 a prepolymer to the slurry. The method 100 also includes a step of mixing 105 a foam mixture of the prepolymer and the slurry and a step of forming a foam layer 107 from the foam mixture. The method 100 of FIG. 1 can be used, in accordance with various embodiments to produce hydrophilic foam layers consistent with many suitable foam compositions, including the various examples described with greater detail below.

The step of forming a slurry 101 can include, for example, mixing a hydrophilic agent, a salt, water and a surfactant or wetting agent together. Other ingredients may be added to the slurry, for example, one or more adjuvants, antimicrobial agents, coloring agents, any other suitable special additives, or combinations thereof. The salt can, in accordance with various embodiments, render the hydrophilic agent more fluid so that it can be blended into the slurry and inhibit the absorbing power of the hydrophilic agent. The salt solution can be added, for example, such that the salt is distributed in the foam in a physiologic amount of about 0.7 to about 1.0% (e.g., 0.85%) by weight when the foam is in its final state, ready to be applied to the wound. It will be apparent in view of this disclosure that, in some embodiments, the salt can be added in different concentrations such as, for example, about 0.1 to about 5% to permit the use of more or less SAP in the slurry. For each of one or more foam layers, the physiologic solutions can, for example, include normal saline, Ringers solution, Tyrodes solution or other recognized medical physiological solutions that contain physiologic amounts of normal body salts or ions.

The hydrophilic agent, in accordance with various embodiments is included in the slurry so as to be incorporated into the foam layer composition to absorb external liquid, such as wound exudate, and to retain such liquid within the foam layer. When applied to a wound, the hydrophilic agent can cooperate with the foam matrix to hold moisture at the surface of the wound. Such configurations permit healing agents exuded by the wound to be concentrated and held at the wound surface. Concurrently, the hydrophilic agent can absorb fluid from the wound to assist thickening of the blood such that, in accordance with various embodiments, the hydrophilic agent serves as a hemostat. The absorption of exudate by the hydrophilic agent, and the subsequent swelling of the agent results in the removal of inflammatory exudates and particles that would otherwise hinder tissue repair or cause eschar formation. Necrotic debris and bacteria are likewise removed as autolysis and chemical debridement is stimulated.

The hydrophilic agent, in accordance with various embodiments can be a highly absorbent polymer, commonly known as a superabsorbent polymer. One measure of polymer absorbency is its fluid uptake capability. Hydrophilic agents suitable for use in the present invention include polymers that are capable of absorbing at least 50 times their weight of water (i.e., polymers having a fluid uptake of at least 50 ml/g). Hydrophilic agents having an even higher fluid uptake, such as of at least about 100 ml/g and even higher, that is, at least about 150 ml/g, 200 ml/g, 300 ml/g, or higher can be used in accordance with various embodiments. Suitable superabsorbent polymers, in accordance with various embodiments can include sodium and aluminum salts of starch grafted copolymers of acrylates and acrylamides and combinations thereof, as well as polyacrylate salts. Of course, other absorbent materials may be used in combination with such highly absorbent polymers, provided the fluid uptake of the overall combination used for the hydrophilic agent is greater than 50 ml/g. When such agents are employed, either alone or in combination, the resulting foam composition desirably has the ability to hold at least about 3 times its weight in liquid to, for example, about 25 time its weight in liquid or more. In accordance with various embodiments, the resulting foam composition will have the ability to tightly hold at least about 3 times its weight in fluid to, for example, about 20 times its weight in fluid or more. As used herein "tightly hold" or "tightly bound" liquid means the relative amount of liquid retained by the sample after compression, as described in detail hereinafter.

These superabsorbent polymers (SAP) can include, but are not limited to, polyacrylates and/or polyacrylamides, or combinations with CMC, calcium alginates, guar, methyl cellulose, ethyl cellulose or other superabsorbent materials or combinations. The hydrophilic polymers can be used alone, or in combination to achieve the desired absorptivity characteristics in the foam composition.

The slurry, in accordance with various embodiments, can include an adjuvant; preferably, a water-soluble adjuvant. The adjuvant can thus be releasably carried by the resulting foam composition for subsequent release to a chosen situs of application. Release of at least a portion of the adjuvant, in accordance with various embodiments, can occur in response to the presence or absorption of an external liquid, such as wound exudate, which can be absorbed by the foam composition.

It will be appreciated in view of this disclosure that not all of the adjuvant is necessarily released (or need it be) in the presence of the external fluid. However, in accordance with various embodiments, the foam layer composition is produced to release a sufficient amount of adjuvant to achieve a predefined, desired result. To that end, it will be appreciated in view of this disclosure that the efficacy of the adjuvant can be realized upon its release from the foam composition to the situs of application. For example, in the case of a wound dressing, the situs is the wound, burn, or the like, itself. Release of the adjuvant thus provides beneficial treatment to the wound. In accordance with various embodiments, the adjuvant may also have hygroscopic properties, thereby adding to the hydrophilic nature of the foam composition.

In accordance with various embodiments the adjuvants are water soluble so that they may be readily released from the composition upon contact of the foam composition with an external liquid. For wound dressing applications, it is also desirable that the adjuvant be capable of contacting skin without adverse side effects. To that end, in accordance with various embodiments, the adjuvant(s) can include a chemical compound that will have the ability to open the skin pores to achieve a demulcent effect to relieve pain and/or irritation and to achieve an emollient effect to soften the skin and prevent maceration. In accordance with various embodiments the adjuvant(s) can also be compatible with therapeutic or other agents which may be carried by the adjuvant for subsequent delivery to the situs of application. Suitable adjuvants, in accordance with various embodiments can include water soluble alcohols, including mono, di and polyhydric alcohols, monols, and diols.

In accordance with various embodiments, one or more of propylene glycol and glycerin can be used as adjuvants. Propylene glycol and glycerin can possess the attributes of a medicament, cosmetic, or therapeutic agent and propylene glycol can also function as a skin enhancer and antimicrobial agent. Thus, when fluid is absorbed by the foam, propylene glycol and glycerin can be released, thereby allowing the hydrophilic agent to swell as it absorbs fluid from the wound and causing the foam to conform to the wound contour.

The amount of adjuvant included in the foam mixture can be sufficient to impart softness and pliability to the foam composition and be capable of delivering a therapeutic agent or the like, if included, to the environment of application. Additionally, the amount of adjuvant can be low enough to avoid weakening or gelling the composition. In accordance with various embodiments, an amount of adjuvant in the foam mixture can be, for example, from about 5 wt. % to about 30 wt. % of the foam mixture.

The slurry can also include various additional medicaments, cosmetics, and therapeutic agents to be carried with the adjuvant and released with it to the desired situs. This configuration permits the transmission of such therapeutic or other agents carried in the adjuvant to the area of application outside the foam composition (e.g., the wound situs), further assisting in the beneficial treatment of the wound.

In accordance with various embodiments, therapeutic or other agents which may be incorporated into the foam composition can include but are not limited to various other agents such as dyes, skin enhancers, antimicrobials, essential oils, herbals, surfactants, other healing agents or combinations thereof, each of which would be incorporated into the slurry. Skin enhancers can include, for example, propylene glycol, glycerin, dipropylene glycol, castor oil, dimethicone, PEG, other water soluble or water insoluble materials, any other suitable skin enhancer, or combinations thereof. Antimicrobials or antiseptics can include, for example, iodine, chlorhexidine gluconate, cationic polymers, PHMB, PCMX, silver, zinc, lactoferrin/xylitol, honey, acetic acid, ascorbic acid, citric acid, any other suitable antimicrobial or antiseptic, or combinations thereof. Essential oils can include, for example, tea tree oil, cinnamon oil, lavender oil, peppermint oil, coconut oil, eucalyptus oil, any other suitable oils, or combinations thereof. Herbals can include, for example, Echinacea, turmeric, bromelain, goldenseal, oak bark extract, pycnogenol, any other suitable herbal, or combinations thereof. Other healing agents can include, for example, niacin, Vitamin E, retinoic acid, aloe, sodium hyaluronate, collagen, organic dyes, other known healing agents, or combinations thereof. In addition to use as a wetting agent as described with greater detail below, surfactants can be included and can be, for example any nonionic surfactants, cationic or anionic surfactants, amphoteric surfactants, detergents, wetting agents or emulsifiers, or combinations thereof. Organic dyes can include, for example, gentian violet, scarlet red, methylene blue, other suitable dyes, or combinations thereof.

The slurry, in accordance with various embodiments, can also include one or more wetting agents and/or surfactants to provide more uniform wettability of the resulting foam. The wetting agent also aids in controlling the cell size of the foam and in the reticulation of the final foam. Wetting agents suitable for use include, for example, non-ionic surfactants. Materials that can be used as the wetting agent, either alone or in admixture, include, for example, block copolymers of ethylene oxide and propylene oxide sold under the trademark PLURONIC by BASF Wyandotte corporation, PLURONIC F-68, PLURONIC F-108, ethoxylated sorbitan fatty acid esters, glycerol esters, polyglycerol esters, and silicone fluids. Such wetting agents can aid in wound cleansing without causing tissue damage. For example, PLURONIC F-68 performs a cleansing action, particularly because a portion of the surfactant may be released when the foam composition is exposed to the exudate of the wound. In accordance with various embodiments, the amount of wetting agent can be, for example, from about 1% to about 10% by weight of the foam mixture. In accordance with various embodiments, the amount of wetting agent can be from about 5% to about 7% by weight. In accordance with various embodiments, the wetting agent does not react with the foam composition or any component of the foam formulation, thereby advantageously avoiding negative impact on foam formation or adverse effects on the desired characteristics of the foam layer composition in use or while being stored.

In accordance with various embodiments, the slurry can also include one or more pH indicators to impart a color change at the variable pH levels of wound fluid. In accordance with various embodiments the amounts of pH indicators can be small enough to render the dressing non-toxic yet high enough to undergo color change as the wound heals and moves from a basic to acidic condition. PH indicators can include but are not limited to methyl red, phenol red, bromocresol purple, p-nitrophenol, bromothymol blue, natural pH indicators such as red cabbage, chlorophenol red, rainbow indicators, brilliant yellow, propyl red, bromocresol green, alizarin red S, neutral red, methyl purple, m-nitrophenol, phenolphthalein, thymolphthalein, any other suitable pH indicator, or combinations thereof. The slurry can also include water. For example, in accordance with various embodiments, the slurry can include one or more of purified water, deionized water, or distilled water.

The slurry can also include a salt. For example, a physiologic salt such as sodium chloride, calcium chloride, potassium chloride, magnesium chloride or others may be incorporated into the slurry. Additionally, saline solutions, Ringers Solution, Tyrodes solution and others can be used in accordance with various embodiments to provide at least a portion of the water and the salt. In accordance with various embodiment, the positive ions of the salts bind sites on the polyacrylate chain of the SAP to inhibit the SAP from absorbing water. This allows mixing of much more superabsorbent polymer into the aqueous phase and, consequently, absorption and retention of much more fluid by the foam layer. In accordance with various embodiments, the salt can also make the foam physiological so that when it is used as a wound dressing it contains the same amount or concentration of electrolytes as the body does. This configuration is advantageous because physiologic products applied to tissue are much more acceptable to the body, are beneficial to wound healing, and cause no negative salt gradients.

The step of adding 103 a prepolymer to the slurry can include adding any suitable prepolymer to the slurry. In accordance with various embodiments, the prepolymer can include a water reactive isocyanate-capped polyether prepolymer. Generally, these prepolymers can be safe for use in the human body, and can be capable of foaming in an aqueous system in the absence of a catalyst. In accordance with various embodiments, the prepolymers do not dissolve in the aqueous liquid. Additionally, in accordance with various embodiments, the prepolymers can cure to form a porous cellular foam matrix to permit both absorption of external fluids and carriage of the chosen adjuvant in the foam composition. Such cellular foam matrices can advantageously provide a large volume available not only for absorption but the containment of the chosen adjuvant. In accordance with various embodiments, the prepolymers can be capable of curing in the presence of water, in the absence of catalyst, and at ambient temperature.

Prepolymers, in accordance with various embodiments can include, for example, isocyanate-capped polyether prepolymers such as those disclosed in U.S. Pat. Nos. 3,903,232 and 4,137,200 each of which is incorporated herein by reference in its entirety. The prepolymers disclosed in U.S. Pat. Nos. 3,903,232 and 4,137,200 have a defined average isocyanate functionality greater than 2. Additionally, the prepolymers disclosed in U.S. Pat. Nos. 3,903,232 and 4,137,200 can be capped with aromatic isocyanates, such as, for example, toluene diisocyanate or methylene diphenyl isocyanate, or with aliphatic isocyanates, such as isophorone diisocyanate.

Suitable isocyanate-capped polyether prepolymers can also include, for example, prepolymers sold under the trademark HYPOL such as FHP 2000, HYPOL FHP 2002, HYPOL FHP 3000. HYPOL 2000, HYPOL 2002 and HYPOL 3000 prepolymers are derived from toluene diisocyanate. FHP 2000 and FHP 2002 both have an equivalent weight (per NCO) of 625, an NCO content of 1.60 meq/g and a specific gravity of 1.19. The viscosity of FHP 2000 is 18,500 cps (Brookfield LVF, #4 Spindle, 12 rpm at 25.degree. C.) and that of FHP 2002 is 20,000. FHP 3000 has an equivalent weight (per NCO) of 425, an NCO content of 2.35 meq/g, a specific gravity of 1.15 and a viscosity (measured as described above) of 10,500.

Suitable isocyanate-capped polyether prepolymers can also include, for example, prepolymers derived from toluene diisocyanate and referred to as AQUAPOL prepolymers, commercially available from Carpenter Corporation. AQUAPOL prepolymers have an NCO-value of 2.5 to 3.0 and are formed from the reaction of toluene diisocyanate and an organic polyether polyol containing at least 40 percent by weight ethylene oxide adducts as described at Col. 2, lines 3-22 of U.S. Pat. No. 4,517,326.

Suitable isocyanate-capped polyether prepolymers can also include, for example, prepolymers derived from toluene diisocyanate and sold under the trademark Optipol. Optipol is commercially available from Essentra.

The amount of prepolymer in the foam mixture used to prepare the hydrophilic foam composition can be determined dependent on a number of factors. For example, the proportion of other components in the foam mixture as will be described in greater detail hereinafter. In general, the amount of prepolymer can be sufficient to form a polyurethane foam, to releasably contain the adjuvant, and to adequately contain the hydrophilic agent. Additionally, in accordance with various embodiments, the ratio of prepolymer to hydrophilic agent can be such that the foam mixture does not degrade or break up into its separate constituents. Furthermore, for example, there can be sufficient prepolymer to provide integrity to the foam matrix but little enough prepolymer that the resulting polyurethane composition does not become unworkable. In accordance with various embodiments, the amount of prepolymer should be such that the resulting foam composition is relatively smooth and soft while exhibiting the desired absorbence characteristics so that it does not irritate or otherwise harm the skin.

The concentration of prepolymer can also depends on its isocyanate functionality and the degree of crosslinking desired in the final foam composition. In general, the greater the isocyanate functionality, the greater the degree of crosslinking in the cured foam matrix. In accordance with various embodiments, the foam mixture can comprise from about 20% to about 60% by weight of prepolymer. In accordance with various embodiments, the foam mixture can comprise from about 45% to about 55% by weight of the prepolymer. In accordance with various embodiments, the prepolymers can be used alone or in combination.

It will be apparent in view of this disclosure that the relative proportion of prepolymer, surfactant (wetting agent), adjuvant, water, salt and hydrophilic agent included in the foam mixture can be varied over wide ranges in order to prepare a hydrophilic foam layer composition having the desired release and exchange characteristics previously described, while likewise providing a foam composition that is aesthetically satisfactory, insofar as its oilyness, touch, appearance and general feel. For use as a wound dressing, for example, it is preferable that the foam composition be soft and generally smooth to the touch so that it does not irritate the skin. These characteristics can be achieved by properly balancing the relative proportion of adjuvant, prepolymer, hydrophilic agent, salt, wetting agent and water.

By way of example, if excess propylene glycol or glycerin is used in the foam mixture (foam mixture) the resulting foam layer composition can require an extended cure time with decreased ability to tightly hold external liquid and may have an oily or spongy non-uniform surface. Conversely, if insufficient propylene glycol or glycerin is included in the foam mixture, the resulting foam layer composition can be less uniform, have relatively poor flow and porosity characteristics, have relatively poor dimensional stability, and absorb liquid at a slower rate.

Furthermore, in accordance with various embodiments, if the relative proportion of prepolymer to hydrophilic agent is too high or too low, the resulting product will not be perform as intended. For example, the amount of hydrophilic agent must be sufficient to absorb the external liquid and to promote the release of the adjuvant. If the amount of hydrophilic agent is too low, there is insufficient absorption of external liquid. Conversely, if the amount of hydrophilic agent is too high, then the viscosity of the foam mixture will be too high for appropriate mixing.

In accordance with various embodiments, a weight ratio of prepolymer to hydrophilic agent in the range of about 20:1 to about 20:15 and a ratio of prepolymer to adjuvant in the range of about 20:1 to about 20:10 can provide a foam composition having suitable liquid release and exchange characteristics as well as being soft to the touch and not oily.

It will likewise be apparent in view of this disclosure that the wetting agent employed and the amount thereof used can affect the characteristics of the resulting foam composition. In accordance with various embodiments, the wetting agent can be used in an amount such that the foam is substantially uniform and readily wettable.

The step of mixing 105 the foam mixture can be performed, for example, by preparing and mixing an organic phase and an aqueous phase together. In accordance with various embodiments, the organic phase comprises the isocyanate-capped prepolymer. In accordance with various embodiments, the aqueous phase comprises the adjuvant, wetting agent, water, salt, the hydrophilic agent and other desired additives, such as, for example, dyes or the like to color the resulting foam. If a medicament, cosmetic or therapeutic agent is included in the foam mixture it can be included in the aqueous phase. To prepare the foam, the organic phase and aqueous phase can be simply mixed at room temperature.

In some embodiments, a composition (foam mixture) for making foam is provided. In some embodiments, any of the compositions for making foam described herein can include, alone or in combination, one or more of an isocyanate-capped polymer-ether prepolymer, a salt, a hydrophilic agent, or water. In some embodiments, any of the compositions for making foam described herein can include, alone or in combination, wherein the prepolymer includes one or more of isocyanate-capped polyether polyols that are water reactive and have an isocyanate equivalent weight of from about 0.5 meq/g to about 5 meq/g, or mixtures thereof. In some embodiments, any of the compositions for making foam described herein can include, alone or in combination, wherein the prepolymer is present in an amount of from about 35 to about 75% by weight of the composition. In some embodiments, any of the compositions for making foam described herein can include, alone or in combination, wherein the salt is isotonic to the human body. In some embodiments, any of the compositions for making foam described herein can include, alone or in combination, wherein the salt is a mineral salt. In some embodiments, any of the compositions for making foam described herein can include, alone or in combination, wherein the salt includes one or more of sodium, calcium, potassium, and magnesium. In some embodiments, any of the compositions for making foam described herein can include, alone or in combination, wherein the salt is present in an amount of from about 0.7 to about 1.0% by weight of the composition.

In some embodiments, any of the compositions for making foam described herein can include, alone or in combination, wherein the hydrophilic agent is capable of absorbing water and having a fluid intake of about at least 50 ml of water per gram of hydrophilic agent. In some embodiments, any of the compositions for making foam described herein can include, alone or in combination, wherein the hydrophilic agent includes one or more of starch grafted copolymers of acetate salts, starch grafted copolymers of acrylamide salts, polyacrylate salts or combinations with CMC, calcium alginate, guar, methyl cellulose, ethyl cellulose, or mixtures thereof. In some embodiments, any of the compositions for making foam described herein can include, alone or in combination, wherein the hydrophilic agent is a polyacrylate salt. In some embodiments, any of the compositions for making foam described herein can include, alone or in combination, wherein the hydrophilic agent is present in an amount from about 6 to about 10% by weight of the composition. In some embodiments, any of the compositions for making foam described herein can include, alone or in combination, wherein the hydrophilic agent is present in the composition in an amount sufficient to provide a foam capable of absorbing at least 2 times, at least 3 times, at least 5 times, at least 10 times, at least 15 times, at least 25 times, or more of its weight of liquid. In some embodiments, any of the compositions for making foam described herein can include, alone or in combination, wherein the ratio of the salt to the hydrophilic agent is about 1:15 to about 1:75 by weight.

In some embodiments, any of the compositions for making foam described herein can include, alone or in combination, wherein an adjuvant is present in the composition. In some embodiments, any of the compositions for making foam described herein can include, alone or in combination, wherein the adjuvant includes an alcohol. In some embodiments, any of the compositions for making foam described herein can include, alone or in combination, wherein the alcohol includes one or more of polyhydric alcohol, isopropyl alcohol, ethanol, propylene glycol, polyethylene glycol, polypropylene glycol, glycerin, 1,2,4-butanetriol, trimethylolpropane, sorbitol, pentaerythritol, or mixtures thereof. In some embodiments, any of the compositions for making foam described herein can include, alone or in combination, wherein the alcohol is present in the composition from about 1 to about 20% by weight of the composition.

In some embodiments, any of the compositions for making foam described herein can include, alone or in combination, wherein a surfactant is present in the composition. In some embodiments, any of the compositions for making foam described herein can include, alone or in combination, wherein the surfactant includes one or more of non-ionic, cationic or anionic surfactants, amphoteric surfactants, detergents, emulsifiers, wetting agents, or combinations thereof. In some embodiments, any of the compositions for making foam described herein can include, alone or in combination, wherein the surfactant is a non-ionic surfactant including one or more of block copolymers of ethylene oxide and propylene oxide, ethoxlyated sorbitan fatty acid esters, glycerol esters, polyglyerol esters, silicone fluids, or mixtures thereof. In some embodiments, any of the compositions for making foam described herein can include, alone or in combination, wherein the surfactant is present in the composition in an amount of about 0.1 to about 20% by weight of the composition.

In some embodiments, any of the compositions for making foam described herein can include, alone or in combination, wherein a skin enhancer is present in the composition. In some embodiments, any of the compositions for making foam described herein can include, alone or in combination, wherein the skin enhancer includes one or more of dipropylene glycol, castor oil, and dimethicone, or mixtures thereof. In some embodiments, any of the compositions for making foam described herein can include, alone or in combination, wherein the skin enhancer is present in the composition in an amount of about 1 to about 10% by weight of the composition. In some embodiments, any of the compositions for making foam described herein can include, alone or in combination, wherein an anti-microbial is present in the composition. In some embodiments, any of the compositions for making foam described herein can include, alone or in combination, wherein the antimicrobial includes one or more of iodine, chlorhexidine gluconate, cationic polymers, PHMB, PCMX, silver, zinc, lactoferrin, xylitol, honey, acetic acid, ascorbic acid, citric acid, or mixtures thereof. In some embodiments, any of the compositions for making foam described herein can include, alone or in combination, wherein the anti-microbial is present in the composition in the amount of about 0.1 to about 10% by weight of the composition.

In some embodiments, any of the compositions for making foam described herein can include, alone or in combination, wherein an essential oil is present in the composition. In some embodiments, any of the compositions for making foam described herein can include, alone or in combination, wherein the essential oil includes one or more of tea tree oil, cinnamon oil, lavender oil, peppermint oil, coconut oil, *eucalyptus* oil, or mixtures thereof. In some embodiments, any of the compositions for making foam described herein can include, alone or in combination, wherein the amount of the essential oil in the composition is about 0.1 to about 10% by weight of the composition.

In some embodiments, any of the compositions for making foam described herein can include, alone or in combination, wherein an herbal therapeutic agent is present in the composition. In some embodiments, any of the compositions for making foam described herein can include, alone or in combination, wherein the herbal therapeutic agent includes one or more of *Echinacea*, turmeric, bromelain, goldenseal, oak bark extract, pycnogenol, or mixtures thereof. In some embodiments, any of the compositions for making foam described herein can include, alone or in combination, wherein a therapeutic agent is present in the composition. In some embodiments, any of the compositions for making foam described herein can include, alone or in combination, wherein the therapeutic agent includes one or more of niacin, Vitamin E, aloe, retinoic acid, sodium hyaluronate, collagen, or mixtures thereof. In some embodiments, any of the compositions for making foam described herein can include, alone or in combination, wherein the amount of the therapeutic agent present in the composition is about 0.1 to about 10% by weight of the composition.

In some embodiments, any of the compositions for making foam described herein can include, alone or in combination, wherein an organic dye is present in the composition. In some embodiments, any of the compositions for making foam described herein can include, alone or in combination, wherein the organic dye includes one or more of scarlet red, gentian violet, methylene blue, or mixtures thereof. In some embodiments, any of the compositions for making foam described herein can include, alone or in combination, wherein a pH indicator is present in the composition. In some embodiments, any of the compositions for making foam described herein can include, alone or in combination, wherein the foam made from the composition is a wound dressing.

The step of forming a foam layer 107 can be performed, for example, by casting or extruding the foam mixture. Thus, the foam layer can, in accordance with various embodiments, be an in situ reaction product of the foam mixture created by adding the prepolymer to the slurry.

In accordance with various embodiments, the liquid foam mixture can be cast onto an appropriate substrate (e.g., film with adhesive, release coated material, spun lace, or combinations thereof), leveled and compressed to suitable thickness during and or after rising of the foam and coiled into rolls. In accordance with various embodiments, uniformity of thickness and density can be obtained by using a final compression after the foam has fully risen but before it has finally cured. This finished wound dressing material can be packaged, sterilized and used as a wound dressing; or converted to different configurations then packaged, sterilized and used as a wound dressing.

Figure 2:
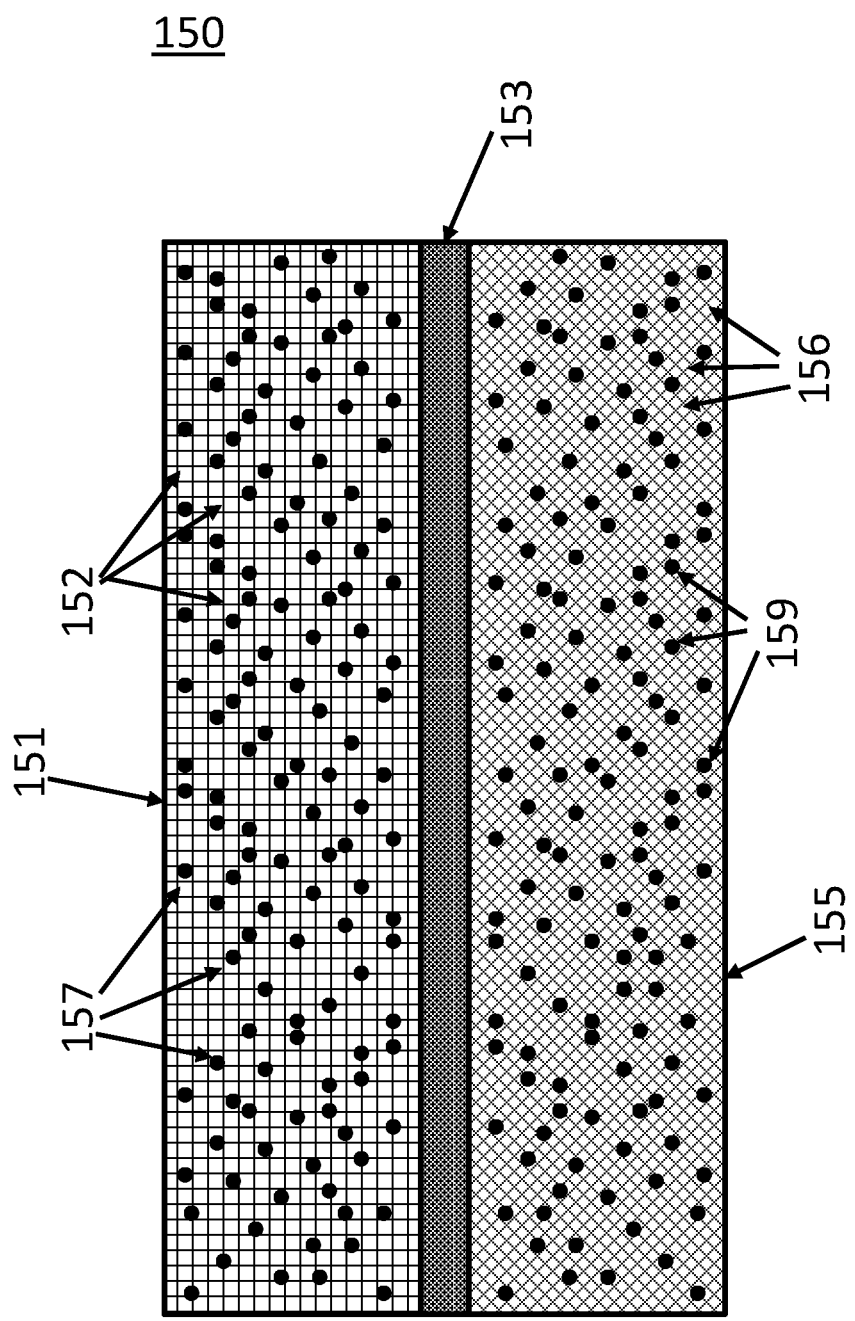
FIG. 2 is a cross-sectional view of a multilayer foam composition in accordance with various embodiments.

Referring now to FIG. 2, the resulting foam layer or, as shown in FIG. 2, each foam layer of a multilayer foam (e.g., formed by the multilayer foam manufacturing processes described below with reference to FIGS. 3-4C) can be a foam material 150 including a polyurethane foam matrix (e.g., first polyurethane foam layer 151 and second polyurethane foam layer 155) having a plurality of pores (e.g., first pores 152 and second pores 156), interchangeably referred to as cells, formed therein. Each of the pores 152, 156 or at least a portion thereof can retain one or more particles (e.g., first particles 157 or second particles 159) therein such that each type of the particles 157, 159 are generally evenly distributed throughout the foam layer 151, 155 in which they are retained. For example, particles 157, 159 retained within the pores 152, 156 can include particles of one or more of the hydrophilic agent, the salt, a medicament, the surfactant, the essential oils, the physiologic agent, the adjuvant, the antimicrobial, the therapeutic, the skin enhancer, or combinations thereof. In accordance with various embodiments, the colorant, dye, or pH indicator can either be retained within the pores 152, 156 or can be bonded to the polyurethane foam matrix itself. In some embodiments, an interface layer 153 (e.g., as discussed with greater detail below with reference to FIGS. 3-7G, can be interposed between the first layer 151 and the second layer 155 for bonding the first and second layers 151, 155 together and for controlling a moisture vapor transmission rate (MVTR) of the foam material 150. As explained with greater detail below, the interface layer 153 can be composed of compressed and/or collapsed polyurethane foam matrix and be formed in-situ during formation of the foam material 150. In accordance with various embodiments, the each layer of the foam material 150 can be, for example about 8 to about 12% water by weight, about 5 to about 9% surfactant (wetting agent) by weight, about 0.1 to about 5% or about 0.5 to about 1.0% salt by weight, about 5 to about 9% adjuvant by weight (e.g., about 2.5 to about 4.5% propylene glycol and about 2.5 to about 4.5% glycerol), about 0.1-0.5% colorant by weight, about 1 to about 20% or about 7 to about 12% SAP by weight, and about 50 to about 70% polyurethane foam matrix by weight.

The foam material 150, in some embodiments, can absorb about 3 to about 25 times the weight of the foam material 150 or about 10 to about 15 times the weight of the foam material 150. The foam material 150, in some embodiments can retain (tightly hold) about 3 to about 20 times the weight of the foam material 150 or about 5 to about 15 times the weight of the foam material 150. These high absorption and retention rates, in accordance with various embodiments result from the high percentage of SAP included in the foam material 150 due to the inclusion of the salt in the slurry. Additionally, the foam itself is hydrophilic as are other ingredients such as the surfactant, propylene glycol, and/or glycerol.

In some embodiments, a foam material can be provided. In some embodiments, any of the foam materials described herein can include, alone or in combination, one or more of a polyurethane foam matrix defining a plurality of pores, a hydrophilic agent retained within at least a portion of the pores for improving an absorption of the foam material, a salt retained within at least a portion of the pores in an amount sufficient to render the foam material isotonic, and a surfactant retained within at least a portion of the pores in an amount sufficient to be released upon contact with a moist surface. In some embodiments, any of the foam materials described herein can include, alone or in combination, one or more of the polyurethane foam matrix is about 50 to about 70% by weight of the foam material, the hydrophilic agent is about 1 to about 20% by weight of the foam material, the salt is about 0.1 to about 5% by weight of the foam material, or the surfactant is about 5 to about 9% by weight of the foam material. In some embodiments, any of the foam materials described herein can include, alone or in combination, water, wherein the water is about 8 to about 12% by weight of the foam material.

In some embodiments, any of the foam materials described herein can include, alone or in combination, an adjuvant retained within at least a portion of the pores. In some embodiments, any of the foam materials described herein can include, alone or in combination, wherein the adjuvant is about 5 to about 9% by weight of the foam material. In some embodiments, any of the foam materials described herein can include, alone or in combination, a colorant retained within at least a portion of the pores or bonded to the polyurethane foam. In some embodiments, any of the foam materials described herein can include, alone or in combination, wherein the colorant is about 0.1 to about 0.5% by weight of the foam material. In some embodiments, any of the foam materials described herein can include, alone or in combination, wherein a pH indicator retained within at least a portion of the pores. In some embodiments, any of the foam materials described herein can include, alone or in combination, wherein the pH indicator is about 0.1 to about 0.5% by weight of the foam material. In some embodiments, any of the foam materials described herein can include, alone or in combination, an antimicrobial retained within at least a portion of the pores. In some embodiments, any of the foam materials described herein can include, alone or in combination, a medicament retained within at least a portion of the pores. In some embodiments, any of the foam materials described herein can include, alone or in combination, a skin softener retained within at least a portion of the pores.

In some embodiments, any of the foam materials described herein can include, alone or in combination, wherein the salt is one of sodium chloride, calcium chloride, potassium chloride, magnesium chloride, saline solutions, Ringers Solution, Tyrodes solution, or combinations thereof. In some embodiments, any of the foam materials described herein can include, alone or in combination, wherein the hydrophilic agent is a superabsorbent polymer. In some embodiments, any of the foam materials described herein can include, alone or in combination, wherein the superabsorbent polymer is one of sodium salts of starch grafted copolymers of acrylates, sodium salts of starch grafted copolymers of acrylamides, aluminum salts of starch grafted copolymers of acrylates, aluminum salts of starch grafted copolymers of acrylamides, polyacrylate salts, or combinations thereof. In some embodiments, any of the foam materials described herein can include, alone or in combination, wherein the hydrophilic agent has a fluid uptake of not less than 50 ml/g. In some embodiments, any of the foam materials described herein can include, alone or in combination, a first surface of the foam material having an embossed or debossed pattern formed thereon.

In use, the hydrophilic foam layer composition, when applied to a moisture laden surface, can absorb moisture from that surface. In accordance with various embodiments, the foam layer composition can additionally release at least a portion of the adjuvant(s) carried by the composition in response to absorption of the moisture. The hydrophilic polyurethane foam layer composition, in accordance with various embodiments, can be implemented as an absorbent pad of an occlusive or semi-occlusive wound dressing, commonly applied to injuries such as abrasions, incisions, punctures, lacerations, ulcers, sores, burns and the like to aid in stopping bleeding and in protecting the wound from contamination.

When applied to a wound, the foam layer composition can absorb and retain a high volume of aqueous fluid (e.g., wound exudate) and release the adjuvant to the wound situs. In accordance with various embodiments, adjuvants and, optionally, additives, such as therapeutic agents, medicaments and the like can be incorporated into the foam and releasably carried. Thus, a wound dressing which incorporates the foam layer composition can be prepared which is advantageously capable of providing enhanced hemostatic and chemical debridement characteristics as well as transdermal, bacteriostatic, emollifying, demulcifying and wound cleansing characteristics.

Once affixed to the skin surface, the foam composition absorbs exudate moisture from the wound. In absorbing the exudate moisture, the foam swells to conform to the wound contour so as to become thermally insulative to the surface of application, while at the same time holding moisture against the surface in order to keep that surface moist. The foam composition will then assist in maintaining a warm, moist and sealed wound with appropriate pH to promote epidermal resurfacing and re-epithelization. A wound dressing which includes the foam composition of the present invention does not adhere to the wound and thus does not cause re-injury upon its removal from the wound. This is believed to be due to the liquid exchange and the maintenance of a moist environment about the wound.

Multilayer Foams

Referring now to FIG. 3, a method 300 is provided for forming a multilayer foam in accordance with various embodiments. The method 300 includes a step of providing 301 a first foam layer. The method 300 also includes a step of casting 303 a foam layer on the first foam layer. The method 300 also includes a step of compressing 305 the second foam layer. The method 300 also includes a step of curing 307 the second foam layer to form a multilayer foam with the first foam layer. In some embodiments, as described below, the step of compressing 305 permits the formation of an interface layer to bond the first and second layers and to provide controllable (e.g., based on the amount and force of compression) moisture vapor transmission rate (MVTR) through the interface layer and, thus, the multilayer foam.

The step of providing 301 a first foam layer can be performed by providing any suitable foam layer. In particular, the step of providing 301 can be performed, for example, but not limited to, by forming a foam layer as described above with reference to FIGS. 1, 2, and 9A-9D.

The step of casting 303 a second foam layer on the first foam layer can be performed, for example, by pouring or otherwise distributing a second foam mixture onto the first foam layer. The second foam mixture can be any suitable mixture for forming a second foam layer and can include any suitable composition or mixture of foam reactants such as, for example, any of the slurry components, prepolymers, addititves, adjuvants, salts, solutions, or other reactants, alone or in any combination, as described above with reference to FIGS. 1, 2, and 9A-9D.

The step of compressing 305 the second foam layer can be performed, for example, using a compressive device or devices such as, for example, one or more horizontal rollers positioned to compress the second foam mixture. For example, the foam layer production lines 400, 420, 450, as illustrated in FIGS. 4A-4C and 5, in accordance with various embodiments, can include a series of horizontal rollers (e.g., rollers 407, 454a, 454b, 501, 503 as shown in FIGS. 4A-4C and 5) for compressing the second foam mixture both before the foam of the second layer is fully risen and after the foam is fully risen, but before it is fully cured. By compressing the second foam mixture in such a manner, as described with greater detail below, control can be provided over both the cured thickness of the multilayer foam and the formation and moisture vapor transmissibility rate (MVTR) of an interface layer formed in-situ between the first and second layers.

Figure 4A:
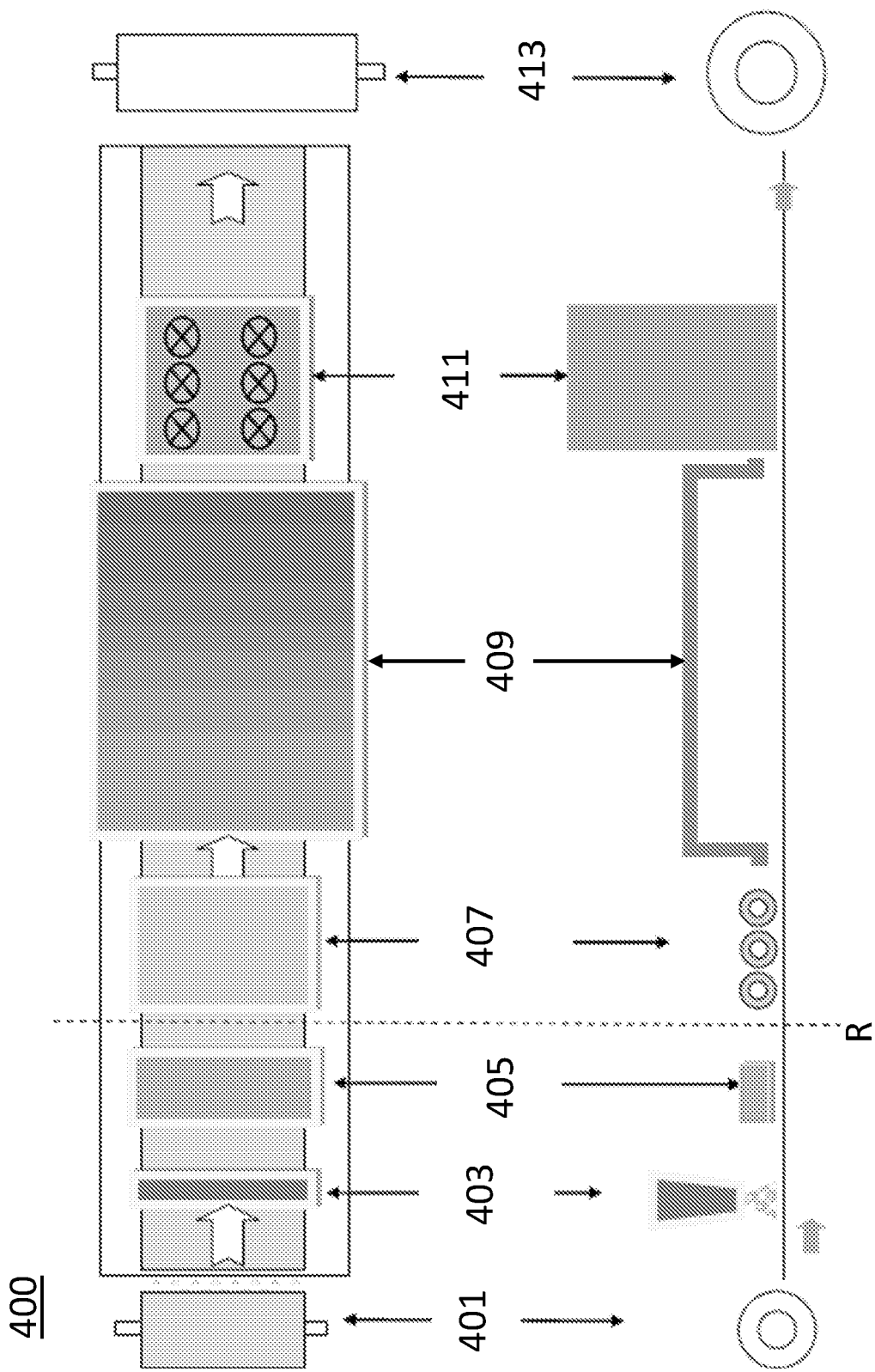
FIG. 4 is a schematic of a production line for forming single or multilayer foams in accordance with various embodiments.
Figure 4B:
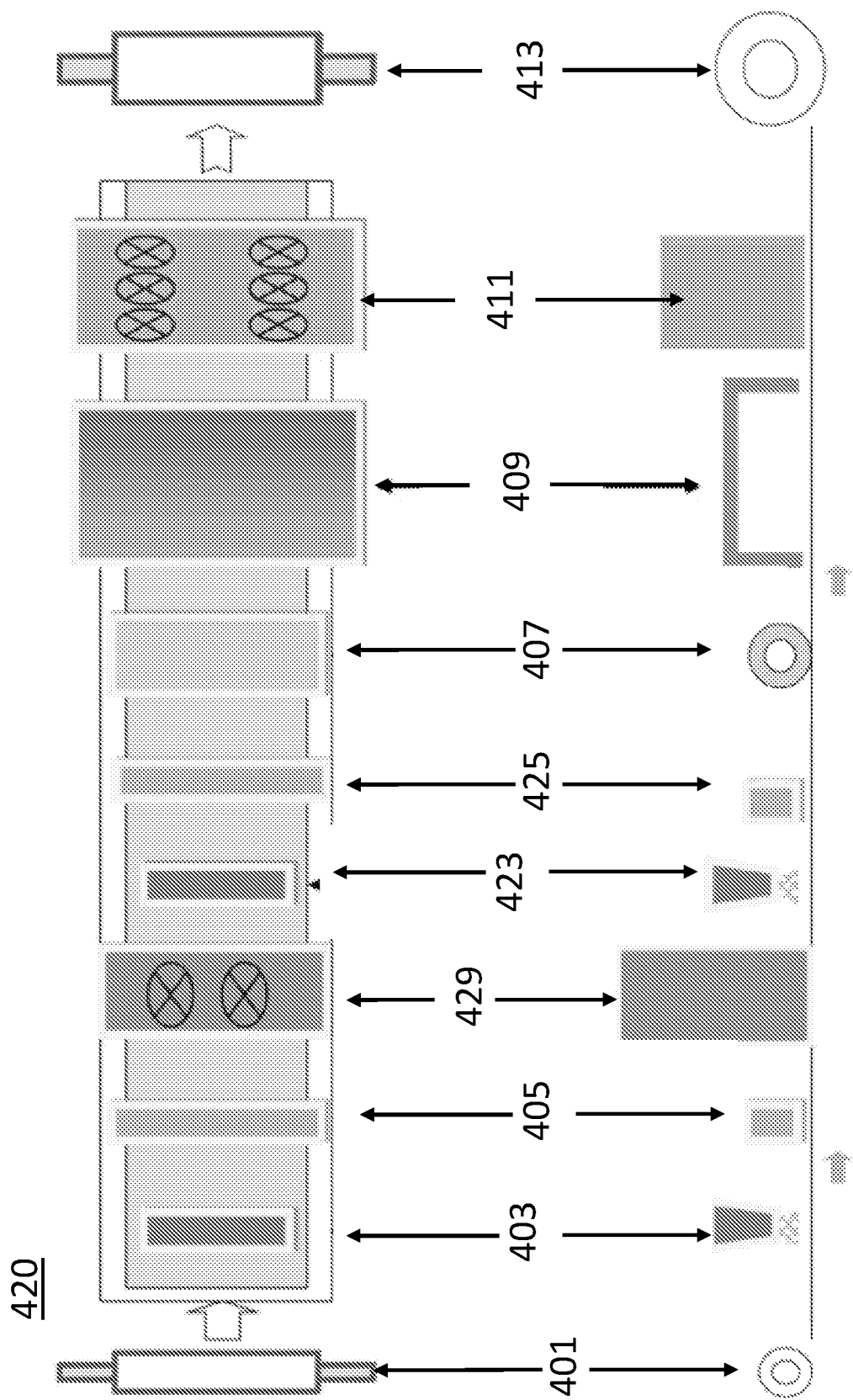
Figure 4C:
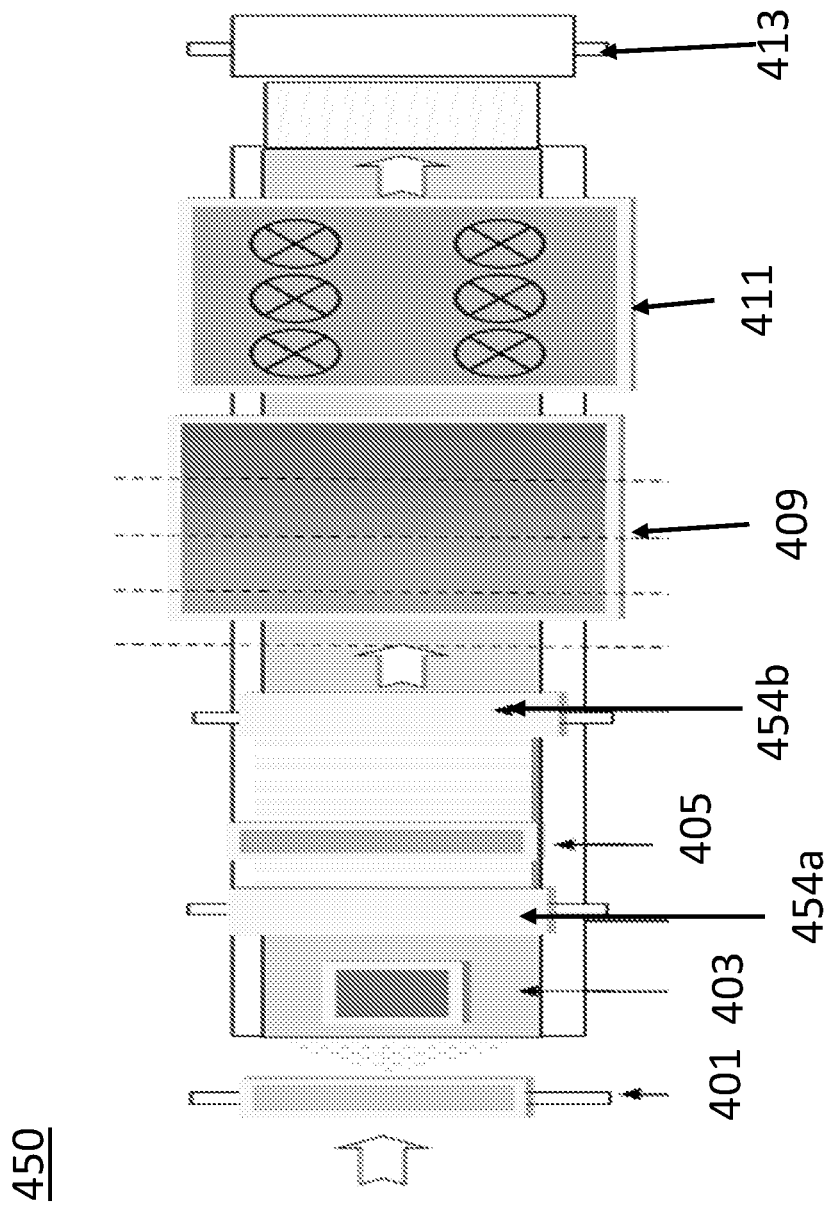

The step of curing 307, the second foam layer to form a multilayer foam can be performed, for example, using one or more of a curing oven (e.g., curing ovens 409, 429 as shown in FIGS. 4A-4C), using dryers or fans (e.g., dryer hood 411 as shown in FIGS. 4A-4C), air drying, or combinations thereof.

Referring now to FIG. 4A, a foam layer production line 400 can include an unwinding roller 401 for providing a substrate on which a foam layer is to be formed and a reactant dispenser 403 for mixing reactants to form a foam mixture (e.g., the first or second foam mixtures described above with reference to FIGS. 1-3) and dispensing the mixture over the substrate. The foam mixture can, for example, be a combination of the slurry and the prepolymer as discussed above. In some embodiments, both the slurry and the prepolymer can be pumped to a static or dynamic mixer chamber, blended therein, then dispensed onto the moving substrate. Through the foam forming process, the foam mixture, in some embodiments, starts as liquid, then becomes a gel, then a tacky gel, then a tacky foam, then a tack free foam, and finally, a cured foam.

The production line 400 also includes levelers and/or spreaders 405 for leveling and compressing the foam mixture while the foam is rising and compression rollers 407 for compressing the foam after rising is complete but before fully curing the foam layer. The production line 400 also includes a curing oven 409 and a dryer hood 411 for completing drying and curing. The production line also includes a winding roller 413 where the cured foam is then wound or coiled onto the winding roller 413 for shipping or further processing.

The unwinding roller 401, in accordance with various embodiments, can be any suitable horizontal roller known in the art capable of providing a substrate on which the foam layer is to be formed to the production line 400. The substrate can be any suitable surface on which the present foam layer can be formed. For example, the substrate for a first or single foam layer, in accordance with various embodiments, can be a film, a film coated with adhesive, a release coated material, paper, waxed paper, spunlace, a polyurethane film, a mylar film, a silicone coated mylar film, any other suitable substrate, or combinations thereof. The substrate can, in some embodiments, subsequently become part of the foam product. For example, the substrate can remain on the foam layer after the foam layer is wound on to the winding roller 413 to prevent the foam from adhering to itself and/or to provide a peelable barrier (e.g., for covering an adhesive coating disposed over a surface of the foam or for maintaining sterility of a wound contact surface of the foam). The substrate can also be adhered to the foam to provide, for example, an outer surface or membrane of a wound dressing. In accordance with various embodiments, the substrate for a second or subsequent layer can be, for example, the first or previous foam layer so that the second or subsequent layer can be formed directly on the first or previous foam layer as described with greater detail below.

The winding roller 413, in accordance with various embodiments, can be any suitable horizontal roller known in the art capable of winding/coiling the foam layer or multilayer foam after curing thereof. In accordance with various embodiments, the winding roller 413 can be similar to the unwinding roller so that, for example, after the winding roller 413 is used to coil the completed first foam layer, it can be repositioned at the beginning of the production line to serve as an unwinding roller 401 in connection with forming of the second foam layer on top of the first foam layer.

The reactant dispenser 403 can include, for example, any suitable device for retaining mixed foam reactants (foam mixture) for distribution over the substrate provided by the unwinding roller 401. Reactant dispensers 403 can include, for example, tubes, hoppers, nozzles, barrels, funnels, chutes, sprayers, any other suitable dispenser, or combinations thereof.

The levelers/spreaders 405 can include any device suitable for spreading and/or leveling the foam mixture while the foam is rising. Levelers and/or spreaders can include, for example, trowels, doctor blades, spreaders, sliding bars, horizontal rollers, any other suitable leveling device, or combinations thereof. The levelers/spreaders 405 can be used, in accordance with various embodiments, to spread and level the foam mixture to ensure even distribution over the substrate and a level surface to produce a consistent foam layer thickness. The levelers/spreaders 405 can also provide compression, optionally in conjunction with compression rollers 407, in order to control the thickness of the foam layer and/or overall multilayer foam. Furthermore, as described with greater detail below, compression by the levelers/spreaders 405 and, optionally, the compression rollers 407 can provide control over the formation and MVTR of an interface layer formed in-situ between the adjacent (e.g., first and second) layers of a multilayer foam.

In FIG. 4A, the point along the production line 400 at which rising of the foam is complete is indicated by dashed line R. The compression rollers 407 can include any suitable horizontal roller or patterned horizontal roller for providing compression to the foam after rising is complete (i.e., after R) but before the foam is fully cured. The compression rollers, optionally in conjunction with levelers/spreaders 405, can provide compression to the foam in order to control the thickness of the foam layer and/or the overall multilayer foam. Furthermore, as described with greater detail below, compression by the levelers/spreaders 405 and/or compression rollers 407 can provide control over the formation and MVTR of an interface layer formed in-situ between the adjacent (e.g., first and second) layers of a multilayer foam. Control of the compression can be achieved by setting a precise height at which the rollers should pass over the foam layer. In accordance with various embodiments, roller height can be controlled such that the compression rollers 407 can be lowered or raised with a precision of 0.001 inches. Still further, compression roller 407 can be used, alone or in conjunction with levelers/spreaders 405, to impart a surface pattern on the foam layer. An example of compression rollers 407 in use is illustrated in FIG. 5.

Figure 5:
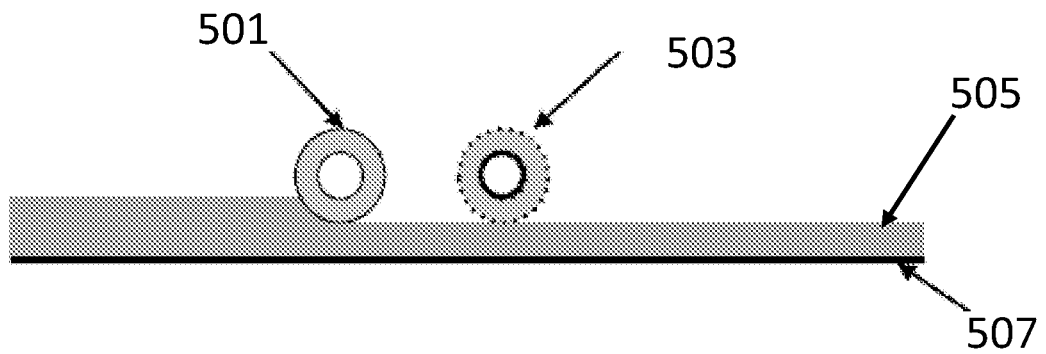
FIG. 5 is a cross-sectional view of a foam layer undergoing compression rolling and surface patterning in accordance with various embodiments.

As shown, in FIG. 5, a first, unpatterned roller 501 initially compresses the foam layer 505, which is being formed on a substrate 507. The compressed portion of the foam layer 505 is then embossed or debossed by a patterned roller 503 to produce a surface pattern of the foam layer 505. Unpatterned roller 501 can include any suitable horizontal roller having a smooth outer surface. Patterned roller 503 can include any suitable horizontal roller having a non-smooth surface. This surface modification can be an aggressive or subtle print pattern, indentation, dimple, or any other conceivable texture. For example, patterns or textures can be produced to improve aesthetic appeal of the foam layer, promote more precise tearing or cutting of the foam layer (e.g., the square grid pattern shown in FIG. 6A), provide one or more regions having a reduced contact surface area (e.g., to reduce bonding to a wound situs as described below), provide an increased absorption surface area for improving an absorption rate of a hydrophilic foam layer (e.g., the dimpled pattern shown in FIG. 6B), any other pattern, or combinations thereof.

Figure 6A:
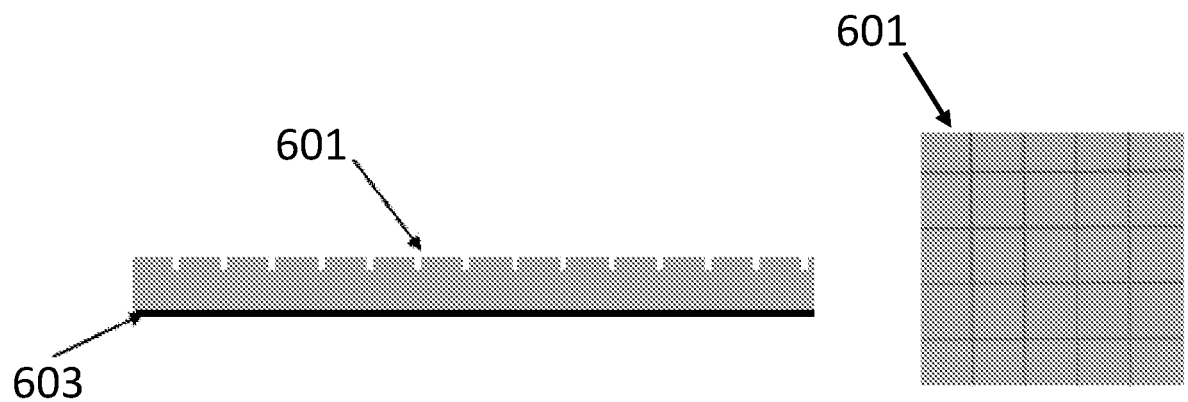
FIGS. 6A-6B are cross-sectional views of surface-patterned foam layers in accordance with various embodiments.

Referring now to FIG. 6A, a patterned foam layer 601 formed over a substrate 603 includes a square grid pattern thereon. The square grid pattern provides guidelines for precisely measuring and cutting the foam layer to a desired size. For example, each square in the square grid can have a predefined length and width. In accordance with various embodiments the length and width can each be, for example, in a range from about 0.1 to about 2.0 inches.

Other patterns can provide different functionality. For example, visual and/or tactile patterns on one side of the foam of a wound care dressing allows a clinician to easily know which side of the dressing to apply to the wound. Additionally, an aggressive texture of raised or recessed areas creates more surface area, thereby resulting in additional absorption sites for taking in wound fluid, thus improving absorption rate. This same type of texture can also create more surface indentations and depressions, thereby diminishing wound surface contact points (of a flat and smooth dressing) and thus decreasing wound adherence upon dressing removal.

Figure 6B:
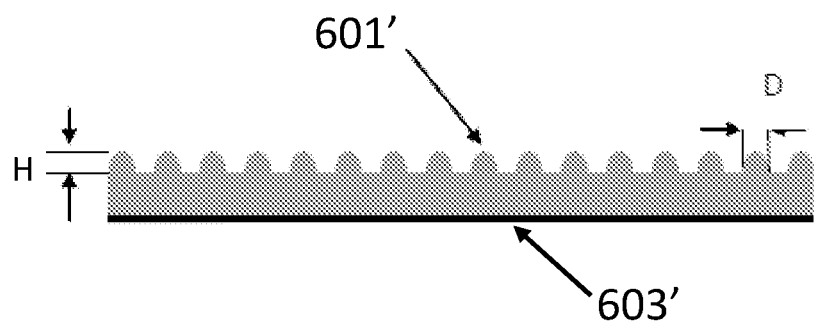

FIG. 6B illustrates patterned foam layer 601' having a dimpled pattern and formed over a substrate 603'. Each dimple has a height H protruding from the outer surface of the foam layer 601' and a diameter D extending along the outer surface of the foam layer 601'. As discussed above, such patterning creates more surface area while reducing the wound contact area, thereby improving absorption rate while decreasing wound adherence upon dressing removal. This effect can be quantified as shown in the table below.

Referring again to FIG. 4A, the curing oven 409 can include any suitable chamber for permitting the foam layer to cure. Curing ovens 409 can, for example, include single zone temperature control, multi-zone temperature control, convection heating systems, hot air impingement, infrared, microwave, any other suitable curing chamber, or combinations thereof.

The dryer hood 411 can be any suitable air-moving device for drying and/or curing the foam. The dryer hood 411 can include, for example, heated dryers, fans, heating systems, cooling systems, a ventilation hood, any other suitable air-moving device, or combinations thereof.

FIG. 4B, in accordance with some embodiments, illustrates a multilayer production line 420. The unwinding roller 401, reactant dispenser 403, levelers/spreaders 405, compression rollers 407, curing oven 409, dryer hood 411, and winding roller 413 can be, for example but not limited to, the same components as described above with reference to FIG. 4A. The multilayer production line 420 also includes a first stage curing oven 429 for at least partially curing the first layer. The first stage curing oven 429 can be, for example but not limited to, similar to curing oven 409. The multilayer production line 420 also includes a second layer reactant dispenser 423 for dispensing the second layer foam mixture. The second layer reactant dispenser 423 can be, for example but not limited to, similar to reactant dispenser 403. The multilayer production line 420 also includes second layer levelers/spreaders 425 for leveling/spreading and/or compressing the second layer foam mixture. The second layer levelers/spreaders 425 can be, for example but not limited to, similar to levelers/spreaders 405.

The configuration of FIG. 4B, in some embodiments, thereby provides for formation of a multilayer foam without a need to form each layer in a separate run through the production line as in FIG. 4A. Rather, after the first layer is initially leveled/spread/compressed by levelers/spreaders 405, the first layer can be at least partially cured by first stage curing oven 429 and then the second layer can be dispensed by second layer reactant dispenser 423 and leveled/spread/compressed by the second layer levelers/spreaders 425 before proceeding to final compression at compression rollers 407, curing oven 409, dryer hood 411, and winding roller 413 as described above with reference to FIG. 4A.

FIG. 4C, in accordance with some embodiments, illustrates an embossing/debossing production line 450. The unwinding roller 401, reactant dispenser 403, levelers/

| Model # | Dimple base diameter (D), mm | Dimple height (h), mm | Dimples surface area per square inches | Surface area per square inches with no dimples | Increase of Surface Area Absoprtion with dimples in (%) | Reduction in wound contact surface Area with Dimaples in (%) |
|---|---|---|---|---|---|---|
| model 1 | 2 | 2 | 2087.39 | 645.16 | 223.55 | 161.26 |
| model 2 | 3 | 2 | 1720.1 | 645.16 | 166.62 | 107.51 |
| model 3 | 2.5 | 2.5 | 2087.39 | 645.16 | 223.55 | 129.01 |
| model 4 | 1.5 | 3 | 3304.6 | 645.16 | 412.21 | 215.01 |
| model 5 | 2.25 | 1.25 | 1609.27 | 645.16 | 149.44 | 143.34 |

As shown in FIG. 4C, embossing or debossing can be imparted to the forming foam by using a patterned cover sheet that spools between a first patterning roller 454a and a second patterning roller 454b (and adheres to the forming foam until it is tack free) or by printing a pattern on the foam prior to curing. Either one creates minor surface indentations and depressions on the surface of the foam layer.

spreaders 405, curing oven 409, dryer hood 411, and winding roller 413 can be, for example but not limited to, the same components as described above with reference to FIG. 4A. The first and second embossing/debossing rollers 454a, 454b can be, for example but not limited to, similar to compression rollers 407, 501, 503 but configured to wind an embossing/debossing film therebetween. The first and second embossing/debossing rollers 454a, 454b are positioned to wind the embossing/debossing film on the surface of the foam layer during the leveling, spreading, compressing, and rising of the foam layer (e.g., by the levelers/spreaders 405). Thus the embossing/debossing production line 450 provides an embossed/debossed foam layer for use in connection with some embodiments.

In accordance with various embodiments, the processes and compositions described above with reference to FIGS. 1-6B can be used to form a multilayer foam as well as providing methods for controlling the breathability of multilayer foams. The multilayer foams may have two or more foam layers formed by adding a first foam layer to a second foam layer wherein the contact of the two layers forms an interface layer. In accordance with various embodiments, breathability of the multilayered foams can be controlled by specifically orienting the interface layer via controlled compression.

The multilayer foam can, for example, be processed by passing through the production line 400 multiple times to make two or more layers of foam cast on top of the preceding layer(s). Alternatively, as shown in FIG. 4B and described above, a multilayer production line can be used to produce the multilayer foam. The multilayer foams can be processed for a second (or third, or more) poured layer using the first (or previous) layer for the substrate. In accordance with various embodiments, the subsequent material can be coiled on full width or slit-to-size rolls. The rolled multilayer foam can, in accordance with various embodiments, be further die-cut to size and packaged individually as wound care dressings.

Referring now to FIGS. 7A-7G, multilayer foams 700 can generally include a first foam layer 701, an interface layer 703, a second foam layer 705, and an optional film 707. The multilayer foam 700, in accordance with various embodiments, can include one or more additional foam layers (e.g., a third layer 709 as shown in FIG. G) which can also introduce one or more additional interface layers (e.g., second interface layer 711 as shown in FIG. G). The interface layer or layers 703, 711, in some embodiments, can eliminate a need for user of an expensive polyurethane or copolymer film as required for conventional foam layer lamination processes.

In accordance with various embodiments, the optional film 707 can, for example include any of the substrates discussed herein above with reference to FIG. 4A-6B, any permeable film, any impermeable film, any breathable film, or combinations thereof. By way of example, the multilayer foam 700, in accordance with various embodiments, can be used as a wound dressing. In accordance with such embodiments, bodily fluids can absorbed from the wound into the multilayer foam 700.

The first foam layer 701 and the second foam layer 705 can be formed according to any of the processes described herein above or as follows and can include any of the compositions or foams previously discussed herein or any other suitable foam layer.

Figure 7A:
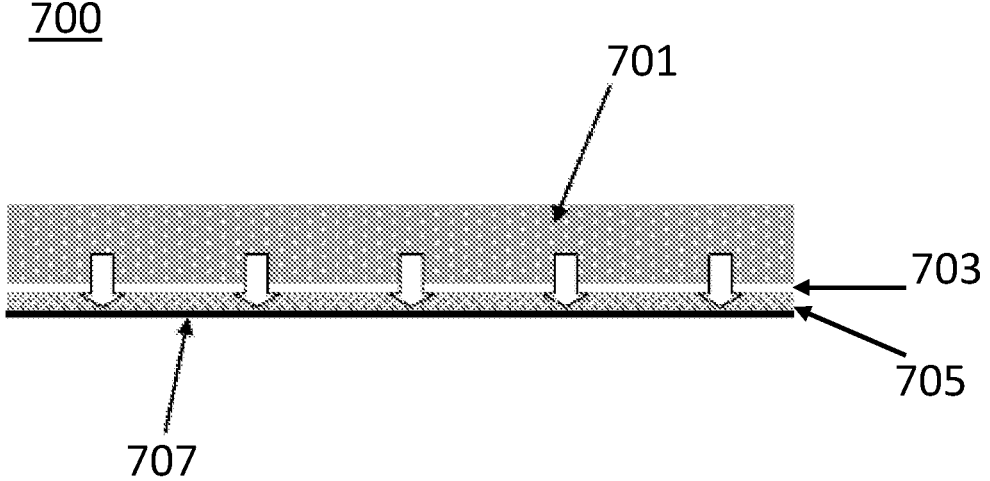
FIGS. 7A-7G are cross-sectional views of multilayer foams having layers of varying thicknesses in accordance with various embodiments.
Figure 7B:
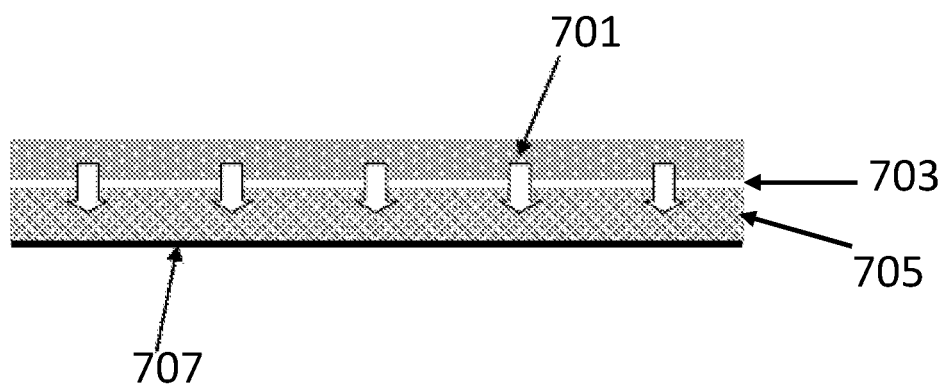
Figure 7C:
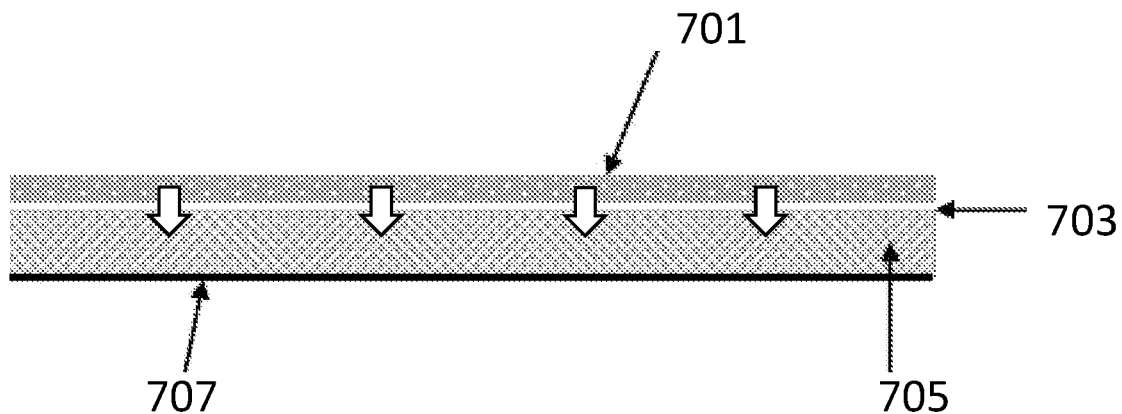
Figure 7D:
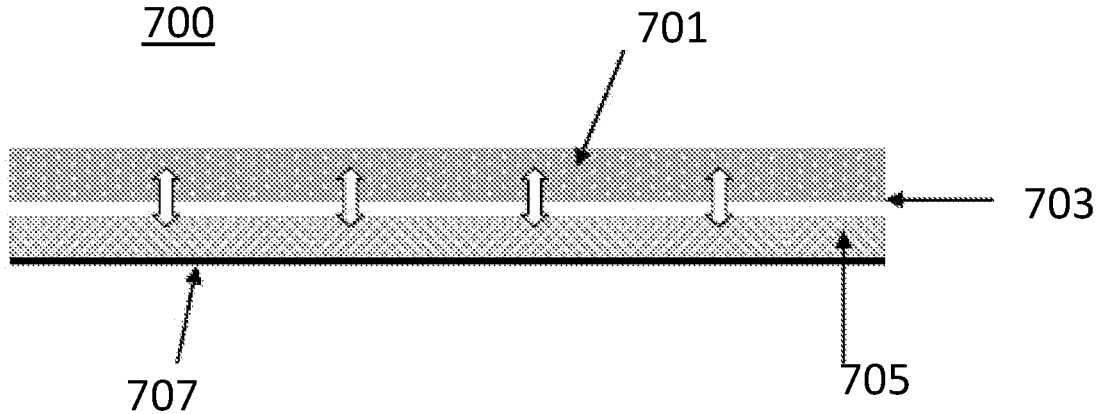
Figure 7E:
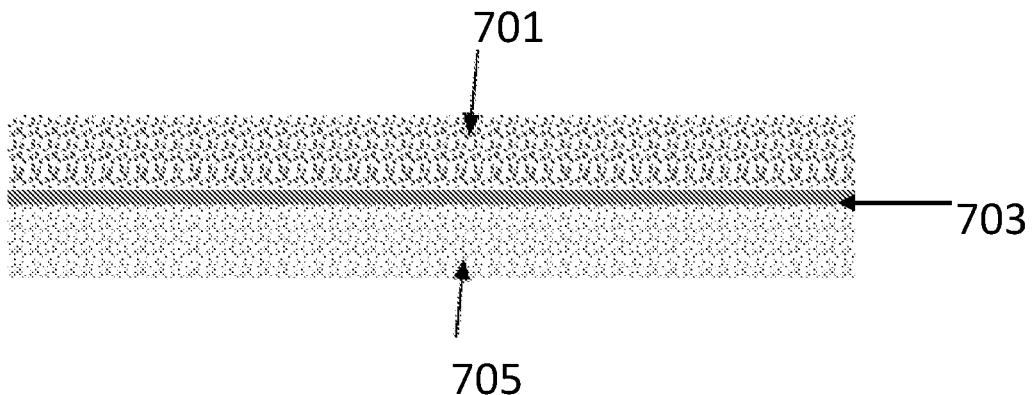
Figure 7F:
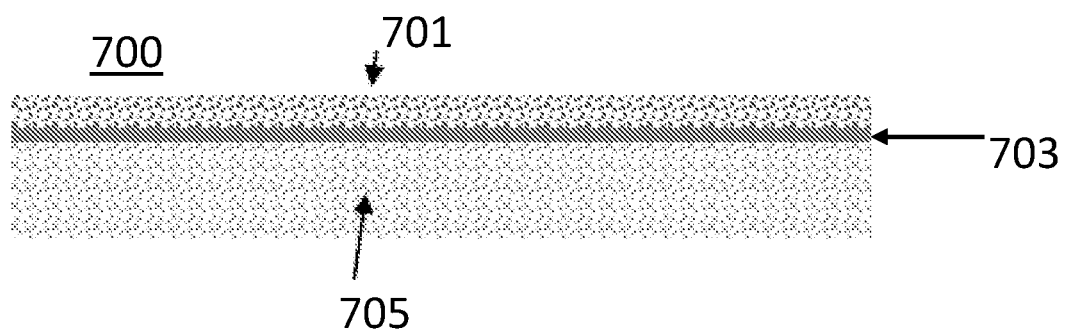
Figure 7G:
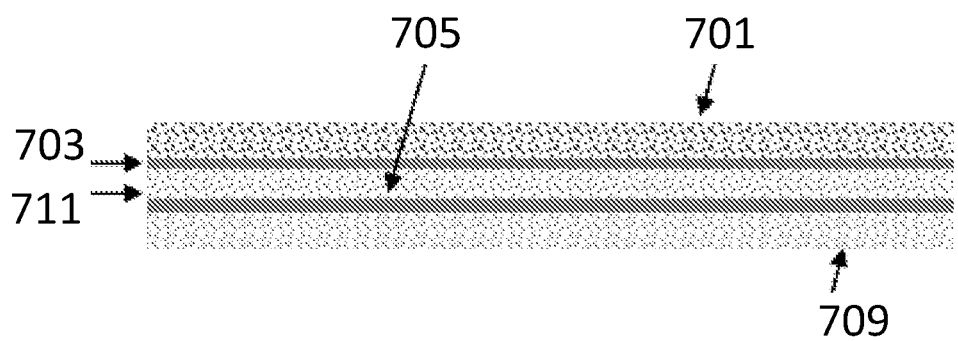

As shown in FIGS. 7A-7G, each of the foam layers 701, 705, 709 of the multilayer foam 700 can be of an independent thickness. For example, in some embodiments e.g., as shown in FIGS. 7D, 7E, and 7G, each of the foam layers 701, 705, 709 can have a same thickness. In some embodiments, e.g., as shown in FIG. 7A, the first layer 701 for placement on a situs (e.g., a wound) can be thicker than a second layer 705 positioned away from the wound. In some embodiments, e.g., as shown in FIGS. 7B, 7C, and 7F, the first layer for placement on a situs (e.g., a wound) can be thinner than a second layer 705 positioned away from the wound. Furthermore, each layer 701, 705, 709 can, for example, have an identical or similar foam composition to one or more of the other layers, or, in accordance with various embodiments, have one or more different compositional components or different concentrations of one or more compositional components as compared to at least one of the other layers.

By permitting such variability of layer thickness and composition, such configurations permit each layer 701, 705, 709 to be customized for a particular purpose. For example, different concentrations or types of medicament, adjuvant, salt, skin conditioners, etc. permit greater control over release of those components into, for example, a wound. Furthermore, the layers 701, 705, 709 can each be customized for softness, conformability, foam strength, foam hydrophilic properties, variable layer colors, other layer properties, or combinations thereof. Thus, for example, a wound contact layer can be soft, pliable, and include high concentrations of skin conditioning agents while a second layer can be stiffer to provide structure while including a higher concentration of SAP for better absorption and including a medicament for metered release into the wound via the interface layer 703.

In accordance with various embodiments, one layer can be an easy release silicone adhesive foam and the second layer an absorptive foam. An outside layer can contain color change components (such as organic dyes or pH indicators), odor control agents such as activated carbon, diffusible microbial control agents such as preservatives, antibiotics or antimicrobials, superabsorbents for greater absorption characteristics in one or more layers, low coefficient of friction or tactile agents such as silicone or silicone compounds, other release agents, various surfactants for wound cleansing or treatment, or any other additives or releasable agents.

The multi-layering (including the interface between them) can further be used to control the release of the active components in accordance with various embodiments. For example, one component can be released faster from a layer close to the skin and a slower release will be achieved for components in a distant layer or layers. In such embodiments, the layer closest to the skin can, for example, contain surfactants and skin moisturizers that aid in easy painless release from the wound bed and periwound. The distant layer can, for example, be thicker and contain superabsorbents that pull and hold moisture away from the skin and prevent maceration. Any additive in either layer can be encapsulated to further control the release time and amount released and to protect various components from reaction or degradation during the manufacturing process.

Casting and compressing the second foam layer 705 on the first foam layer 701 (e.g. by performing the steps of casting 303 and compressing 305 as described above with reference to FIG. 3) to form the multilayer foam 700 results in creation of the interface layer 703 in situ between the first layer 701 and the second layer 705.

The interface layer 703 is generally comprised of bubbles that are compressed, crushed, deflated or broken during the foam forming process. This interface layer 703 therefore limits the amount of moisture that transpires through the dressing. The interface layer 703 is permeable to oxygen, carbon dioxide and other gasses. The interface layer 703 also controls the breathability of the multilayer foam 700, which can be adjusted based on the compositions of the first and second layers 701, 705 and on the timing and parameters of compression during forming of the second layer. In some embodiments, the interface layer 703 can be about 0.001 inches to about 0.100 inches thick or about 0.001 inches to about 0.010 inches thick.

In accordance with various embodiments, the interface layer 703 forms in situ due to tacky liquid foaming mixture material contacting the foam layer substrate (i.e., the first or prior foam layer) and irreversibly bonding to it. The resulting interface layer 703 is semipermeable which adds properties to the overall product such as limiting the liquid exchange, allowing a variable diffusion rate of layer components, and MVTR (moisture vapor transmission rate) yet allowing full transmission of gases such as oxygen and carbon dioxide. The permeability and diffusion rate of the interface layer 703 can be controlled, for example, by applying compression force from the spreaders/levelers 405 and/or the compression rollers 407 on the forming cast foam, by varying the chemistry of the layers; by varying the density or thickness of the successive layers, by using rollers with needles (for layer perforation), protrusions, recesses, or patterns; by using laser perforation; by using heated rollers, by any other suitable means, or combinations thereof.

The interface layer 703 can range in moisture vapor transmission rates (MVTR) from about 1000 to about 4000 grams per square meter per day. In accordance with various embodiments, higher MVTRs permit more moisture to be transferred away from the wound site such that the dressing does not have to be changed as often. However, if MVTR is too high the foam dressing can allow wounds to dry out which can result in the dressing sticking to the wound and causing pain and reinjury when removed. Accordingly, in some embodiments, the MVTR can be about 1500 to about 3000 grams per square meter per day.

In accordance with various embodiments, breathability or MVTR of the interface layer 703 can be controlled by compressing the first layer 701, the second layer 705, and the interface layer 703 before curing, wherein the interface layer controls the breathability between the first and second layers 701, 705.

In accordance with various embodiments, the multilayer foam 700 can have an overall thickness of about 0.050 inches to about 0.500 inches or about 0.200 inches to about 0.220 inches. In accordance with various embodiments, the interface layer 703 can have a thickness of about 0.001 inches to about 0.100 inches or about 0.001 inches to about 0.010 inches. Since the interface layer is formed by crushed, deflated or broken foam cells, it does not necessarily add thickness to the overall foam. The target thickness foam of one layer can range, for example, from 0.150 to 0.200 inches.

In some embodiments, components of the second foam layer are deposited on the first foam layer separately and then can be mixed, spread, and leveled directly on the first foam layer. The leveled components, in accordance with various embodiments can be allowed to partially, but not completely rise and pass through a compression zone where varying compression ratios are utilized to compress the foam formed from the components, finally compressing the foam to a required thickness after it has fully risen, curing the combination of the first foam layer and the new foam layer and drying the same.

By controlling the permeability, the diffusion rate of the multilayered foam, and the rate of release of any loaded agents retained therein, multilayer foams can be customized for various applications. Controlling the MVTR at the interface layer 703 permits the multilayer foam 700 to be versatile and to be configured to have a favorable moisture vapor transmission rate (MVTR) between the wound and environment. The breathability of the multilayer foam 700 can, for example, be based on the characteristics of a wound requiring treatment. For example, if the breathability is too high moisture transpires completely through the dressing to the surroundings or to the patient's clothing. Conversely, if breathability is too low, macerated tissue can develop and delay healing. Thus, different multilayer foams can be used to treat various types of wounds. Furthermore, it will be apparent in view of this disclosure that multilayer foams are not limited to medical or wound care applications. Rather, multilayer foams can be used in any application where multiple layers of foam with multiple components and variable thicknesses can be useful.

In accordance with various embodiments, the interface layer 703 limits the MVTR. Thus, the interface layer 703 can delay the absorption of fluid to the second layer 705 until the first layer 701 becomes saturated. Such functionality can prevents a releasable component in the second layer 705 from diffusing too quickly. Similarly, such functionality can prevent a pH indicator in the second layer 705 from being affected by absorbed exudate or blood until the saturation of the first layer 701. In particular, blood and serum typically have a pH of 7.3 to 7.4. The pH of infected wounds is typically above pH of 8. Thus, a properly selected pH indicator can change color at higher (more basic) pH to indicate the presence of an infected exudate. Furthermore, strong antimicrobials or antiseptics can be contained in the layer away from the wound. In this way they remain non-cytotoxic to the wound while killing microbes absorbed into the foam. Thus healthy tissue in the wound is protected from toxic effects of strong or high concentrations of antimicrobials or other chemicals and the cytotoxins that are generated when bacteria and other microbes are killed are contained within the second (non-contact) layer 705.

Formation of the interface layer 703 can also obviate the need for an expensive polyurethane or copolymer film to be separately applied by adhesive or heat lamination such as those used and described in connection with U.S. Patent Publication 2005/0013987, which is incorporated herein in its entirety. With the multiple layer cast process (e.g., as described herein above), a range of MVTRs are possible without the use of thin polyurethane or copolymer films.

Figure 8A:
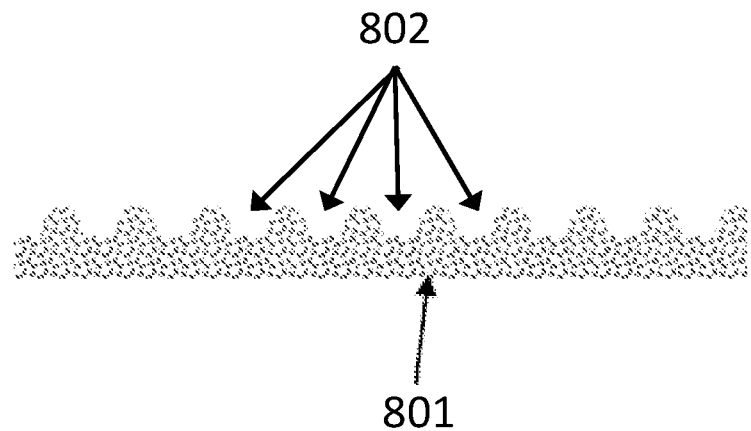
FIGS. 8A-8C are cross-sectional views of illustrating progressive stages of forming a multilayer assembly having a plurality of reservoirs formed therein in accordance with various embodiments.
Figure 8B:
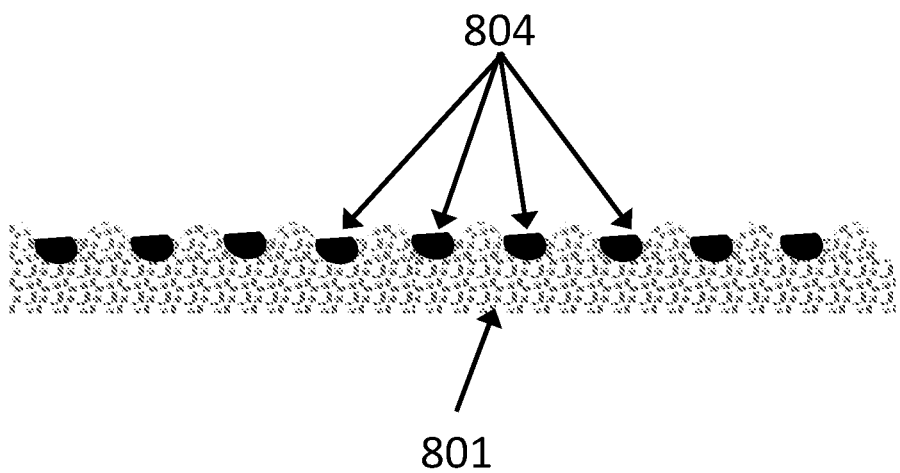
Figure 8C:
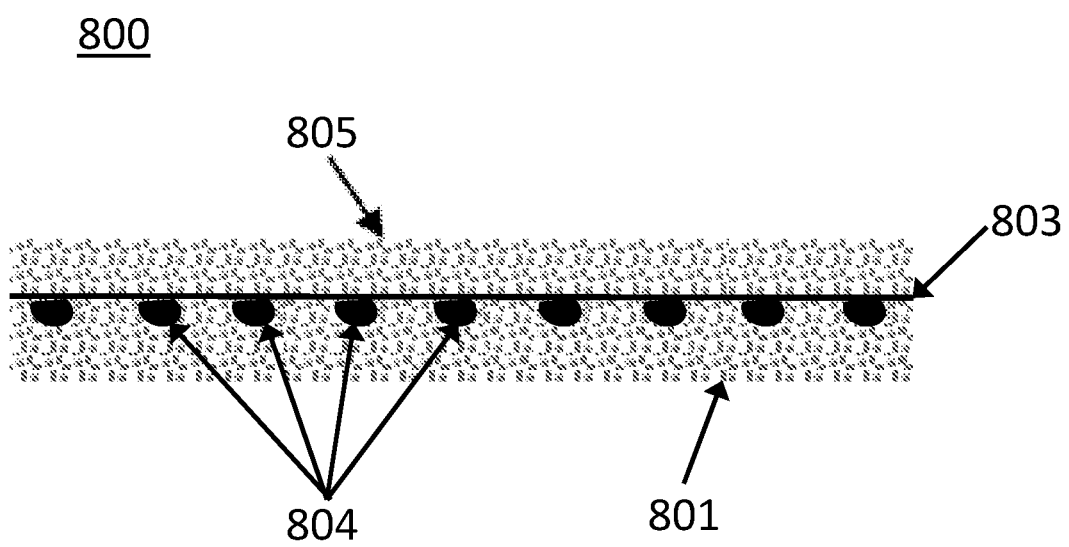

Referring now to FIGS. 8A-8C, in some embodiments, inclusions 802 can be integrated within a multilayer assembly 800. In some embodiments, the multilayer assembly 800 can include a first foam layer 801. In some embodiments, the first foam layer 801 can optionally have one or more recesses 802 formed on a surface thereof. One or more inclusions 804, in accordance with various embodiments, can then be deposited onto a surface of the first layer 801 or into the recesses 802 of the first layer 801. A second foam layer 805 can then be cast on top of the first layer 801 (e.g., as described above with reference to FIGS. 3-7G), thereby forming an interface layer 803 between the first layer 801 and the second layer 805 for bonding the first and second layer and for controlling an MVTR of the multilayer assembly 800 as described herein above.

In accordance with various embodiments, the first layer 801 can, for example but not limited to, be similar to foam layers 151, 505, 601, 601', and 701 as described herein with reference to FIGS. 2, 5, 6A, 6B, and 7A-7G. In accordance with various embodiments, the second layer 805 can, for example but not limited to, be similar to foam layers 151, 505, 601, 601', and 705 as described herein with reference to FIGS. 2, 5, 6A, 6B, and 7A-7G. In accordance with various embodiments, the interface layer 803 can, for example but not limited to, be similar to interface layers 153 and 703 as described herein with reference to FIGS. 2 and 7A-7G.

The recesses 802 can be formed using any suitable methodology, including, for example but not limited to, patterning, embossing, or debossing as described above with reference to FIGS. 4A-6B. Adding the recesses 802 (e.g., by texturing, patterning, embossing, or debossing) the surface of the first layer 801 before adding the inclusions 802 can increase the surface area and provide deeper cavities than open pores/cells of the foam matrix would provide alone. Thus the recesses 802 are better able to contain the deposited inclusions 802 prior to formation of the second layer 805

The inclusions 804, in accordance with various embodiments, can be any materials or ingredients such as, for example, therapeutic agents, antimicrobial agents, super absorbents, surfactants, hemostatic agent, adhesives, any other material capable of being deposited, sprayed or spread on a surface of the first layer 801 or into the recesses 802 of the first layer 801 before forming the second layer 805 thereon. The inclusions 804 can be in any suitable forms or phase such as, for example, liquid, powder, or granulates. In accordance with some embodiments, the inclusions 804 can be provided to and deposited on the first layer 801 or in the recesses 802 by one or more of tubes, hoppers, hoses, nozzles, barrels, funnels, chutes, sprayers, injectors, spreaders, any other suitable supply line or dispenser, or combinations thereof.

Because the second layer 805 is formed directly on the filled first layer 801, the inclusions 804 will be integrated into the multilayer assembly 800. In accordance with various embodiments, such configurations permit the addition of materials that mix poorly with the foam slurry or the pre-polymer, would otherwise interfere with the foam reaction, or would otherwise extend or slow the foam reaction.

Foam Layer Composition Examples

The methods and materials of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

The slurry (aqueous) mixture was prepared from the following components:

| Component | Amount in grams (to nearest 0.01 gram) |
|---|---|
| Water | 400.0 |
| F68 surfactant | 50.0 |
| Sodium chloride | 6.0 |
| Propylene glycol | 25.0 |
| Glycerol | 25.0 |
| Scarlet Red colorant | 0.1 |
| Superabsorbent Polymer 1161 (SAP) | 75.0 |

The procedure to make the slurry:

The water was weighed to the nearest 0.01 grams in the aqueous vessel. 50 grams of F68 surfactant were added and mixed. The surfactant was allowed to fully dissolve, which took about four hours at room temperature without constant stirring. When dissolved 6 grams of sodium chloride were added and dissolved. 25 grams of propylene glycol and 25 grams of glycerin were added and mixed to a uniform solution. The scarlet red was added and allowed to dissolve and mix overnight. The superabsorbent was added with stirring until it began to gel (about 60 seconds), then allowed to sit for three hours to outgas.

46.4 grams of uniform slurry mixture were weighed into the reactant vessel. To this 35.8 grams of Nanopol 700 were added. As soon as they were combined, the mixture was agitated for 20 seconds with a paint mixer attached to a drill at maximum speed. The resulting mix was poured onto a polyurethane film substrate, covered with silicone coated mylar film and rolled 2 times with a 7 pound roller. The material was allowed to sit for 6 minutes before the mylar was removed. The resulting polyurethane foam sheet at about 0.125 inch thick was cut and allowed to cure before drying to 10% moisture. The foam sheet was rolled and stored for testing.

At 10% moisture, the final salt content is about 0.87%; the physiological content of sodium chloride in blood.

Example 2

The slurry (aqueous) mixture was prepared from the following components:

| Component | Amount in grams (to nearest 0.01 gram) |
|---|---|
| Water | 375.0 |
| F68 surfactant | 50.0 |
| Sodium chloride | 5.0 |
| Propylene glycol | 25.0 |
| Glycerol | 25.0 |
| Scarlet Red colorant | 0.1 |
| Chlorhexidine gluconate, 20% solution | 25.0 |
| Superabsorbent Polymer 1161 | 75.0 |

The procedure to make the slurry:

The water was weighed to the nearest 0.01 grams in the aqueous vessel. 50 grams of F68 surfactant were added and mixed. The surfactant was allowed to fully dissolve, which took about four hours at room temperature without constant stirring. When dissolved 5 grams of sodium chloride were added and dissolved. 25 grams of propylene glycol and 25 grams of glycerin were added and mixed to a uniform solution. The scarlet red was added and allowed to dissolve and mix overnight. Next 25 grams of 20% CHG solution was added with stirring until fully distributed. The superabsorbent was added with stirring until it began to gel (about 60 seconds), then allowed to sit for three hours to outgas.

46.4 grams of uniform slurry mixture were weighed into the reactant vessel. To this 35.8 grams of Nanopol 700 were added. As soon as they were combined, the mixture was agitated for 20 seconds with a paint mixer attached to a drill at maximum speed. The resulting mix was poured onto a polyurethane film substrate, covered with silicone coated mylar film and rolled 2 times with a 7 pound roller. The material was allowed to sit for 6 minutes before the mylar was removed. The resulting polyurethane foam sheet at about 0.125 inch thick was cut and allowed to cure before drying to 10% moisture. The foam sheet was rolled and stored for testing.

After drying to 10% moisture, the resulting foam has a CHG content of 0.7%. The CHG foam was found to have a significant Zone of Inhibition for various organisms per the Kirby-Bauer ZOI test, indicating a leaching antimicrobial foam.

Example 3

The slurry (aqueous) mixture was prepared from the following components:

| Component | Amount in grams (to nearest 0.01 gram) |
|---|---|
| Water | 400.0 |
| F68 surfactant | 50.0 |
| Sodium chloride | 5.0 |
| Propylene glycol | 25.0 |
| Glycerol | 25.0 |
| Scarlet Red colorant | 0.1 |
| Nano-crystalline zinc oxide | 7.0 |
| Superabsorbent Polymer 1161 | 75.0 |

The procedure to make the slurry:

The water was weighed to the nearest 0.01 grams in the aqueous vessel. 50 grams of F68 surfactant were added and mixed. The surfactant was allowed to fully dissolve, which took about four hours at room temperature. When dissolved, 5 grams of sodium chloride were added and dissolved. 25 grams of propylene glycol and 25 grams of glycerin were added and mixed to a uniform solution. The scarlet red was added and allowed to dissolve and mix overnight. Next 7.0 grams of nano-crystalline zinc oxide were added with stirring until fully distributed. The superabsorbent was added with stirring until it began to gel (about 60 seconds), then allowed to sit for three hours to outgas.

46.5 grams of uniform slurry mixture were weighed into the reactant vessel. To this 35.8 grams of Nanopol 700 were added. As soon as they were combined, the components were vigorously mixed for 20 seconds with a paint mixer attached to a drill at maximum speed. The resulting mix was poured onto a polyurethane film substrate, covered with silicone coated mylar film and rolled 2 times with a 7 pound roller. The material was allowed to sit for 6 minutes before the mylar was removed. The resulting polyurethane foam sheet at about 0.125 inch thick was cut and allowed to cure and dry. The foam sheet was rolled and stored for testing.

After drying to 10% moisture, the resulting foam has a zinc oxide content of 1.1%. The ZnO foam was found to have a Zone of Inhibition for various organisms per the Kirby-Bauer ZOI test.

Example 4

The slurry mixture was prepared from the following components:

| Component | Amount in grams (to nearest 0.01 gram) |
|---|---|
| Lactated Ringer's Solution | 400.0 |
| F68 surfactant | 50.0 |
| Propylene glycol | 25.0 |
| Glycerol | 25.0 |
| Scarlet Red colorant | 0.1 |
| Superabsorbent Polymer 1161 | 75.0 |

The procedure to make the slurry:

The lactated Ringer's Solution was weighed to the nearest 0.01 grams in the aqueous vessel. 50 grams of F68 surfactant were added and mixed. The surfactant was allowed to fully dissolve, which took about four hours at room temperature. When dissolved, 25 grams of propylene glycol and 25 grams of glycerin were added and mixed to a uniform solution. The scarlet red was added and allowed to dissolve and mix overnight. The superabsorbent was added with stirring until it began to gel (about 60 seconds), then allowed to sit for three hours to outgas.

46.5 grams of uniform slurry mixture were weighed into the reactant vessel. To this 35.8 grams of Nanopol 700 were added. As soon as they were combined, the components were vigorously mixed for 20 seconds with a paint mixer attached to a drill at maximum speed. The resulting mix was poured onto a polyurethane film substrate, covered with silicone coated mylar film and rolled 2 times with a 7 pound roller. The material was allowed to sit for 6 minutes before the mylar was removed. The resulting polyurethane foam sheet at about 0.125 inch thick was cut and allowed to cure and dry. The foam sheet was rolled and stored for testing.

Example 5

The slurry mixture was prepared from the following components:

| Component | Amount in grams (to nearest 0.01 gram) |
|---|---|
| Ringer's Solution, non-lactated | 400.0 |
| F68 surfactant | 50.0 |
| Propylene glycol | 25.0 |
| Glycerol | 25.0 |
| Scarlet Red colorant | 0.1 |
| Superabsorbent Polymer 1161 | 75.0 |

The procedure to make the slurry:

The Ringer's Solution was weighed to the nearest 0.01 grams in the aqueous vessel. 50 grams of F68 surfactant were added and mixed. The surfactant was allowed to fully dissolve, which took about four hours at room temperature. When dissolved, 25 grams of propylene glycol and 25 grams of glycerin were added and mixed to a uniform solution. The scarlet red was added and allowed to dissolve and mix overnight. The superabsorbent was added with stirring until it began to gel (about 60 seconds), then allowed to sit for three hours to outgas.

46.5 grams of uniform slurry mixture were weighed into the reactant vessel. To this 35.8 grams of Nanopol 700 were added. As soon as they were combined, the components were vigorously mixed for 20 seconds with a paint mixer attached to a drill at maximum speed. The resulting mix was poured onto a polyurethane film substrate, covered with silicone coated mylar film and rolled 2 times with a 7 pound roller. The material was allowed to sit for 6 minutes before the mylar was removed. The resulting polyurethane foam sheet at about 0.125 inch thick was cut and allowed to cure and dry. The foam sheet was rolled and stored for testing.

Example 6 Zero Salt Slurry

The slurry mix slurry mixture was prepared from the following components:

| Component | Amount in grams (to nearest 0.01 gram) |
|---|---|
| Water | 400.0 |
| F68 surfactant | 50.0 |
| Propylene glycol | 25.0 |
| Glycerol | 25.0 |
| Scarlet Red colorant | 0.1 |
| Superabsorbent Polymer 1161 | 3.0 |

The procedure to make the slurry:

The water was weighed to the nearest 0.01 grams in the aqueous vessel. 50 grams of F68 surfactant were added and mixed. The surfactant was allowed to fully dissolve, which took about four hours at room temperature. When dissolved, 25 grams of propylene glycol and 25 grams of glycerin were added and mixed to a uniform solution. No salt of any type was added to the aqueous solution. The scarlet red was added and allowed to dissolve and mix overnight. The superabsorbent was added in one gram amounts and thoroughly mixed, then allowed to sit for three hours.

After one gram of SAP was added, it was noted that the slurry was fluid and flowable, with a viscosity below 200 cPs. After the second gram was added, the solution began to gel but was still fluid and flowable, with a viscosity of ~200 cPs. One more gram was added for a total of three grams of SAP. The solution was much thicker but retained flow characteristics. The viscosity was measured at 1850 cPs. A final gram of SAP was added and made the solution gel with minimal flow. The viscosity was measured at 5700 cPs. This gelled material was considered non-pumpable.

40.2 grams of uniform slurry of the 3 grams of SAP (still flowable) intermediate mixture were weighed into the reactant vessel. To this 35.8 grams of Nanopol 700 were added. As soon as they were combined, the components were vigorously mixed for 20 seconds with a paint mixer attached to a drill at maximum speed. The resulting mix was poured onto a polyurethane film substrate, covered with silicone coated mylar film and rolled 2 times with a 7 pound roller. The material was allowed to sit for 6 minutes before the mylar was removed. The resulting polyurethane foam sheet at about 0.125 inch thick was cut and allowed to cure and dry. The foam sheet was rolled and stored for testing.

It was noted that the foam formed was more fluid than other examples and that the rolled foam had an uneven appearance with particulates.

Sample Density, Absorption and Retention Testing

The following tests were performed using the following equipment, materials, and procedures:

Equipment and Materials:

Electronic balance with accuracy to +/−0.01, Caliper with accuracy to +/−0.001, drying oven, cutting tool and 1 inch template, ss tweezers, 100+ ml cups, distilled water, and test material.

Test Method:
1. Cut a 1×1 inch representative sample from the test material using the cutting tool and template. Place in a labeled cup and put in the drying oven for one hour.
2. Remove from oven and measure and record thickness using the caliper to closest 0.001 inch.
3. Weigh the sample to the nearest 0.01 gram and record as W1.
4. Add 50 g distilled water to the empty cup and add sample making sure the sample gets covered with fluid.
5. Allow the sample to sit for 24 hours in static condition.
6. Remove the sample from the distilled water using the tweezers. Hold with tweezers over cup for 10 seconds, shake once, then place on balance and record total absorption weight as W2.
7. Place the wet sample between single paper towel layers and roll forward and back 5 times. Each time position the sample so that it is in a dry area of top and bottom paper towels.
8. Reweigh the sample for retention weight, record as W3.
9. Note whether the sample has delaminated from the film before or during the retention testing.
10. Calculations:

Density in pounds/cubic foot: W1/thickness×3.81

Total absorption: W2−W1 in grams

Total absorption times the original sample weight: W2−W1/W1

Total retention: W3−W1 in grams

Total retention times the original weight: W3−W1/W1

Additional Testing:

% Moisture

A sample is taken, weighed t the nearest 0.01 g and placed in a drying oven. After at least 3 hours at 60° C. remove sample from oven and reweigh to nearest 0.01 g. Calculate weight loss as % moisture.

Absorption Rate

Add 0.1 cc distilled water and time the absorption rate with a stopwatch. Record the rate to the nearest second.

Although the test was performed using distilled water, it will be apparent in view of this disclosure that the test can be performed using distilled water or normal saline (0.9% NaCl).

The test results are illustrated by the tables provided in FIGS. 9A-9D. In particular, FIG. 9A illustrates comparative results between the example compositions described above. FIG. 9B illustrates comparative results between a composition of the subject invention to various conventional foams. FIG. 9C illustrates comparative results between various antibacterial compositions of the subject invention. FIG. 9D illustrates comparative viscosity data between various compositions of the subject invention.

As shown in FIG. 9B, the composition of the subject patent application outperforms the conventional foam dressings. In particular, the composition of the subject invention both absorbs more and tightly retains more fluid than the conventional dressings. Furthermore, the absorption rate of the composition of the subject invention is also faster than or similar to the conventional foams.

FIGS. 9A and 9C document test results of various formulations made according to the examples above. In FIGS. 9A and 9C the core dressing corresponds to Example 1. Example 2 is the targeted 0.5% CHG sample in FIG. 9C. Example 3 is the targeted 1.0% ZnO of FIG. 9C. Example 4 is the lactated Ringers Solution samples made in two different thicknesses in FIG. 9A. Example 5 corresponds to the Ringers Solution non-lactated samples in FIG. 9A. Example 6 corresponds to the zero salt slurry sample in FIG. 9A. The zero salt slurry sample exhibits the lower absorption and retention results that occur when salt is not included in the formula. When there is no salt, far less SAP can be incorporated in the slurry. Without salt, the SAP will disadvantageously preferentially gel all the water, sharply raising the viscosity of the slurry to the point it is not fluid or pumpable.

As shown in FIG. 9D, all 5 viscosity samples included the common slurry components: water, F68 surfactant, glycerol, propylene glycol, and red colorant. Only the salt and SAP were varied. As shown above, Sample 5 was most fluid with best flow capability and Sample 4 was a solid with no fluidity. Thus, viscosity is a function of the percentage of water, NaCl and SAP. In particular, as salt is increased the viscosity decreases if SAP is kept constant. Thus, Sample 4, which had the lowest ratio of salt (1:45) behaved like a mixture without salt, where the water is totally absorbed and the slurry will not flow.

MVTR and Compression Testing of Multilayer Foam

As discussed above, in accordance with various embodiments, two or more foam layers can be bonded together as the foam is cast while simultaneously forming, in situ, an interface layer having a controllable MVTR. The MVTR of the interface layer can be controlled, in accordance with various embodiments, by the number and severity of the compressions. MVTR can also be controlled by altering foam densities, chemistries, textures or other properties between layers.

As shown in the table below, two trials were performed as follows: rollers 1 through 4 are used on foam as it is rising. All are within 6 feet of the pour point. Roller 5 is located about 30 feet from the foam pour point. At this location the foam has completed rising and is tack free but it is not fully cured.

The stages in foam making include a cream time of ~20 seconds where it goes from liquid to gel, a rise time of ~200 seconds where it goes from tacky gel to tacky foam, a tack free time of ~400 seconds, an initial cure time of less than 10 minutes, and a final cure after 24 hours.

| Trial | Compression roller | Gap on first pass, inches | Gap on second pass, inches | Final product thickness, inches | Final product density, lb/CF | Final product MVTR, g/M2/24 hours |
|---|---|---|---|---|---|---|
| 1 | 1 | 0.030 | 0.055 | | | |
|   | 2 | .050 | .070 | | | |
|   | 3 | .045 | .060 | | | |
|   | 4 | .030 | .055 | | | |
|   | 5 | .100 | .075 | 0.195 | 13.5 | 3200 |
| 2 | 1 | .030 | .090 | | | |
|   | 2 | .275 | .275 | | | |
|   | 3 | .275 | .275 | | | |
|   | 4 | .275 | .275 | | | |
|   | 5 | .275 | .290 | 0.270 | 10.0 | 2200 |

As shown in the table, in a test of two similar layers of foam, the highest density (more and severe compressions) resulted in the highest MVTR of 3200 g/M2/day. The lowest density foam (compressed by first roller only) had the lowest MVTR of 2200 g/M2/day. Thus, even with less compression, the interface layer provided a stable bond with high MVTR performance.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Also, the phraseology and terminology used herein is for the purpose of description and should not be regarded as limiting.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for the use of the ordinal term) to distinguish the claim elements.

What is claimed is:

1. A multilayer foam comprising:
a first layer of foam material comprising:
  a first polyurethane foam matrix defining a plurality of first pores;
  a first hydrophilic agent retained within at least a portion of the plurality of first pores for improving an absorption property of the foam material;
  a first salt retained within at least a portion of the plurality of first pores in an amount sufficient to render the first layer of foam isotonic; and
  a first surfactant retained within at least a portion of the plurality of first pores in an amount sufficient to be released upon contact between the first layer of foam material and a moist surface;
one or more secondary layers of foam material, each comprising:
  a secondary polyurethane foam matrix defining a plurality of secondary pores;
  a secondary hydrophilic agent retained within at least a portion of the plurality of secondary pores for improving an absorption property of the foam material;
  a secondary salt retained within at least a portion of the plurality of secondary pores in an amount sufficient to render the one or more secondary layers of foam material isotonic; and
  a secondary surfactant retained within at least a portion of the plurality of secondary pores in an amount sufficient to be released upon contact between the one or more secondary layers of foam material and a moist surface; and
one or more interface layers each bonding at least one of the first layer of foam material and one of the one or more secondary layers of foam material or bonding adjacent the one or more secondary layers of foam material, each interface layer including compressed or collapsed polyurethane foam matrix from at least one of the first layer of foam material or the one or more secondary layers of foam material.

2. The multilayer foam of claim 1, wherein:
the first polyurethane foam matrix is 50 to 70% by weight of the first layer of foam material;
the first hydrophilic agent is about 1 to 20% by weight of the first layer of foam material;
the first salt is 0.1 to about 5% by weight of the first layer of foam material;

the first surfactant is 5 to about 9% by weight of the first layer of foam material;

the secondary polyurethane foam matrix is 50 to 70% by weight of the one or more secondary layers of foam material;

the secondary hydrophilic agent is 1 to 20% by weight of the one or more secondary layers of foam material;

the secondary salt is 0.1 to 5% by weight of the one or more secondary layers of foam material; and the secondary surfactant is 5 to 9% by weight of the one or more secondary layers of foam material.

3. The multilayer foam of claim 1, wherein a moisture vapor transmission rate (MVTR) of the multilayer foam is determined by an MVTR of the one or more interface layers.

4. The multilayer foam of claim 1, wherein at least one of the first layer or the one or more secondary layers includes one or more of an adjuvant, a colorant, a pH indicator, an antimicrobial, a medicament, a skin softener, or combinations thereof retained within at least a portion of the plurality of first pores or the plurality of secondary pores.

5. The multilayer foam of claim 1, a first external surface of the multilayer foam having an embossed or debossed pattern formed thereon.

* * * * *